United States Patent
Ovadia

(10) Patent No.: US 9,364,511 B2
(45) Date of Patent: Jun. 14, 2016

(54) ANTIVIRAL PREPARATIONS OBTAINED FROM A NATURAL CINNAMON EXTRACT

(75) Inventor: Michael Ovadia, Kfar Saba (IL)

(73) Assignee: RAMOT AT TEL-AVIV UNIVERSITY LTD., Tel Aviv (IL)

(*) Notice: Subject to any disclaimer, the term of this patent is extended or adjusted under 35 U.S.C. 154(b) by 2251 days.

(21) Appl. No.: 11/472,537

(22) Filed: Jun. 22, 2006

(65) Prior Publication Data

US 2006/0275515 A1    Dec. 7, 2006

Related U.S. Application Data

(63) Continuation-in-part of application No. PCT/IL2004/001161, filed on Dec. 23, 2004.

(60) Provisional application No. 60/531,985, filed on Dec. 24, 2003.

(51) Int. Cl.
    *A61K 36/00*    (2006.01)
    *A61K 36/54*    (2006.01)
    *A61L 2/16*     (2006.01)

(52) U.S. Cl.
    CPC .. *A61K 36/54* (2013.01); *A61L 2/16* (2013.01)

(58) Field of Classification Search
    None
    See application file for complete search history.

(56) References Cited

U.S. PATENT DOCUMENTS 4,402,950 A    9/1983  Wolf et al.
5,554,596 A *  9/1996  Mach et al.

FOREIGN PATENT DOCUMENTS

| EP | 0 259 617 A2  | 8/1987  |
| EP | 0 870 507 A1  | 10/1998 |
| EP | 0 870 570 A1  | 10/1998 |
| EP | 1 146 111 A1  | 10/2001 |
| JP | 06199674 A    | 7/1994  |

OTHER PUBLICATIONS

Kalemba et al., "Antibacterial and antifungal properties of essential oils". *Curr. Med. Chem.*, vol. 10(10), pp. 813-829, 2003.
Khan et al., "Cinnamon improves glucose and lipids of people with type 2 diabetes". *Diabetes Care*, vol. 26, pp. 3215-3218, 2003.
Lai et al., "Antimicrobial and chemo-preventive properties of herbs and spices". *Curr. Med. Chem.*, vol. 11(11), pp. 1451-1460, 2004.
Mau et al., "Antimicrobial effect of extracts from Chinese Chive, Cinnamon, and Corni fructus". *J. Agric. Food Chem.*, vol. 49, pp. 183-188, 2001.
Qin et al., "Cinnamon extract prevents the insulin resistance induced by a high fructose diet". *Horm. Metab. Res.*, vol. 35, pp. 119-125, 2004.
Tabak et al., "Cinnamon extracts' inhibitory effect on *Helicobacter pylori*". *J. Ethnopharmacol.*, vol. 67, pp. 269-277, 1999.
Valero et al., "Antibacterial activity of 11 essential oils against *Bacillus cereus*, in tyndallized carro broth". *Intl. J. of Food Microbiology*, vol. 85, pp. 73-81, 2003.
Velluti et al., "Impact of essential oils on growth rate, zearalenone and deoxynivalenol production by *Fusarium graminearum* under different temperature and water activity conditions in maize grain". *J. of Applied Microbiology*, vol. 96, pp. 716-724, 2004.
Velluti et al., "Inhibitory effect of cinnamon, clove, lemongrass, oregano and palmarose essential oils on growth and fumonism B1 production by *Fusarium proliferatum* in maize grain". *Intl. J. of Food Microbiology*, vol. 89, pp. 145-154, 2003.
Lin et al., "Anti-herpes virus type 2 activity of herbal medicines from Taiwan". *Pharmaceutical Biology*, vol. 41(4), pp. 259-262, 2003.
Takechi et al., "Structure and antiherpetic activity among the tannins". *Phytochemistry*, vol. 24(10), pp. 2245-2250, 1985.
Kurokawa et al., "Antipyretic activity of cinnamyl derivatives and related compounds in influenza virus-infect mice". *European Journal of Pharmacology*, vol. 348, pp. 45-51, 1998.
Agarwal et al., "Phytochemical and pharmacological investigations of genus cassis: a review". *Asian Journal of Chemistry*, vol. 11(2), pp. 295-299, 1999.
M. Premanathan, "A survey of some Indian medicinal plants fro anti-human immunodeficiency virus (HIV) activity". *Indian Journal of Medicine Research*, vol. 112, pp. 73-77, 2000.
Big Thesaurus of Traditional Chinese Drug (Part I), Shanghai Sciene & Technology Publishing House, 1986, pp. 890-892, 1st Edition, China Jiangsu New Medical College.
Portari Mancini, D.A., et al., "Antioxidantes do extracto aquoso da canela . . . ", Revista Brasileira de Ciencias Farmaceuticas / Brazilian Journal of Pharmaceutical Sciences, vol. 35, No. 1, pp. 155-160, (1999).
Kainuma, M., et al., "The efficacy of a herbal medicine (Mao-to) in combination with intravenous natural . . . ", Phytomedicine, vol. 9, pp. 365-372, (2002), Urban & Fischer Verlag.
Chao, S.C., et al., "Screening for Inhibitory Activity of Essential Oils on Selected Bacteria, Fungi and Viruses", J. Essent. Oil Res., vol. 12, pp. 639-649, (2000), Allured Publishing Corp.
Broadhurst, et al., "Insulin-like Biological Activity of Culinary and Medicinal Plant Aqueous Extracts in Vitro", J. Agric. Food Chem., vol. 48, pp. 849-852, (2000).

* cited by examiner

*Primary Examiner* — Qiuwen Mi
(74) *Attorney, Agent, or Firm* — Browdy and Neimark, P.L.LC.

(57) ABSTRACT

The present application provides a natural aqueous extract obtainable from a cinnamon bark (*Cinnamon* sp.) which has antiviral activity against enveloped viruses including influenza A, Parainfluenza (Sendai) virus and HSV-1 viruses, as well as in vivo activity in inhibition of Influenza A and Parainfluenza viruses. The present application also concerns a method for the extraction of said cinnamon extract and applications thereof.

41 Claims, 25 Drawing Sheets

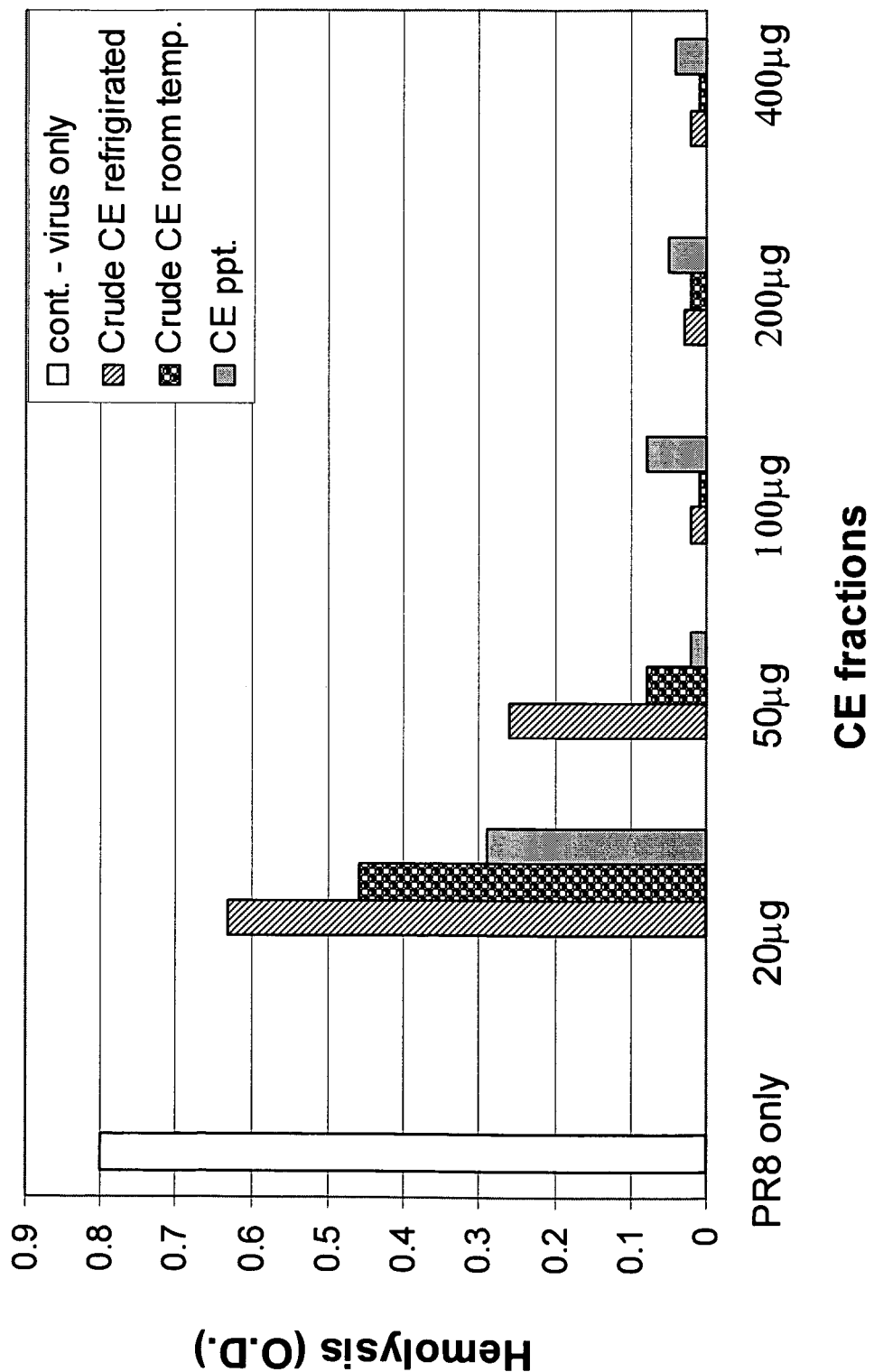

ANTIVIRAL PREPARATIONS OBTAINED FROM A NATURAL CINNAMON EXTRACT

This application is a Continuation In Part of PCT application No. PCT/IL2004/001161 of Dec. 23, 2004, and claims the benefit of U.S. Provisional Patent Application No. 60/531, 985, filed Dec. 24, 2003, the contents of all listed applications being hereby incorporated in their entirety.

FIELD OF THE INVENTION

The present invention concerns an antiviral preparation obtained from a plant extract.

BACKGROUND OF THE INVENTION

Viruses are important pathogens of both humans and animals. Outbreak of a virus infection often results from introduction of a new virus (such as HIV, West Nile Virus, SARS), or from introduction of a new strain of a well known virus to an immunologically naïve population, e.g. influenza.

Despite the importance of the recent outbreaks of West Nile Virus and SARS, influenza is still one of the most prevalent and significant viral infections. Although the availability of formalin-inactivated trivalent vaccines has reduced the impact of influenza epidemics, this virus is still associated with significant morbidity and mortality worldwide. It infects 10-20% of the total population during seasonal epidemics, resulting in between three to five million cases of severe illness and at least 250,000 to 500,000 deaths each year worldwide (World Health Organization, W.H.O., Global Influenza Program, September 2003 and W.H.O. Fact Sheet, March 2003). In the U.S.A. alone, more than 100 million cases are reported each year, causing 20,000 deaths and a consequent strong economic impact, estimated at around 22.9 billion dollars for 1995 (American Lung Association, 2002). W.H.O. has estimated the total burden at around 71-167 billion dollars per year (W.H.O. Fact Sheet, March 2003).

Until recently, amantadine and rimantadine were used for the treatment of influenza infection, but these are now believed to be associated with severe adverse effects (including delirium and seizures which occur mostly in elderly persons on higher doses). When used for prophylaxis of pandemic influenza at lower doses, such adverse events are less apparent. In addition, the virus tends to develop resistance to these drugs (Steinhaur et al., 1991).

A new class of antivirals, the neuraminidase inhibitors, has recently been developed. Such drugs as zanamivir and oseltamivir, which have fewer adverse side effects (although zanamivir may exacerbate asthma or other chronic lung diseases) are nevertheless expensive and currently not available for use in many countries (W.H.O. Fact Sheet, March 2003). Influenza may develop resistance to neuraminidase inhibitors too (McKimm-Berschkin, 2000; Gubavera, et al. 2002).

Many herbs and spices, among them also cinnamon, have been shown to feature antimicrobial and chemoprotective activities, (Lay and Roy, 2004). Extracts from cinnamon obtained by organic solvents (for example as in Velluti et al, 2004), typically contain the following ingredients: Eugenol (82%), Caryophylene (4.6%), Eugenyl acetate (2.1%), Linalool (1.8%), Cinnamaldehyde (1%), Cinnamyl alcohol acetate (1%), 2-Propyl benzodioxol (1%), and Cubebene (<1%). These extracts, which are in fact essential oils, have shown to exhibit antifungal activity. (Velluti et al., 2003 and Velluti et al, 2004).

Other cinnamon bark essentials oils had antibacterial activity against *Bacillus cereus*, (Valero and Salmeron, 2003); as well as antibacterial and antifungal activities, (Kalemba and Kunicka, 2003 and Mau et al., 2001).

Cinnamon hydrophobic fractions extracted in organic solvents had antibacterial activity against *Helicobacter pylori*, (Tabak, M. et al., 1999); antifungal activity for fungi causing respiratory tract mycoses, (Singh, H. B. et al., 1995), and anti HIV-1 activity caused by inhibiting the reverse transcription, (Yamasaki et al., 1998).

Compounds obtained from cinnamon are also used for other indications such as the use of cinnamon powder for reducing serum glucose triglycerides, LDL cholesterol and total cholesterol, (Khan et al, 2003); water extracts of cinnamon were used as antioxidants (Murcia et al, 2004); were shown to prevent insulin resistance, (Qin et al., 2004); and were also shown to inhibit $Na^+/K^+$ ATPase and $Cu^{2+}$ ATPase, (Usta et al., 2003). Essential oil extract obtained from cinnamon were further shown to improve digestion (Hernandez et al., 2004).

SUMMARY OF THE INVENTION

The present invention is based on the surprising finding that a natural aqueous extract from a cinnamon bark (*Cinnamon* sp.) has antiviral activity against enveloped viruses including influenza A, Parainfluenza (Sendai) virus and HSV-1 viruses, as well as in vivo activity in inhibition of Influenza A and Parainfluenza viruses in mice.

By a preferred embodiment of the invention, isolated active fraction of cinnamon bark (hereon referred to as CE) having antiviral activity, has in addition one or more of the following chemical properties:
1. It is precipitated by various chloride salts such as KCl, NaCl, $MgCl_2$, $SrCl_2$, $CuCl_2$, or $ZnCl_2$.
2. It exhibits absorbance at 280 nm of 15 O.D/mg. cm.
3. It maintains most of its activity after incubation in 0.1M NaOH, or 0.1M HCl, or 0.1M $H_2SO_4$.
4. It can be extracted into an aqueous solution without need for organic solvents in a relatively inexpensive and simple manner.
5. It can be maintained for a long period of time (at least two years) as a stable powder or in solution in a refrigerator or at room temperature;
6. It is heat-stable and can thus be sterilized at temperature up to at least 134° C.

The term "CE ppt" as used hereon refers to the extract isolated fraction obtained by salting out with KCl 0.15M.

As regards the biological activity, the CE of the invention is capable of inhibiting viruses at room temperature, within a few minutes of administration, and at relatively low levels. Thus in addition to the pharmaceutical use, this immediate inhibition, at room temperature and at low levels enables also surface disinfections of suspected contaminated areas or purifying circulating air.

The CE of the present invention are effective against both influenza and Parainfluenza viruses as well as against HSV-1 viruses and may protect infected human erythrocytes and other erythrocyte cells from the activity of viruses pre-absorbed on the erythrocytes. Thus, the CE of the present invention may be considered as effective treatment of cells already pre-absorbed with the virus. Furthermore, pre-absorption of the CE of the invention onto cells has a prophylactic effect in protecting the cells from subsequent viral infection.

By one aspect the present invention concerns a novel aqueous extract of cinnamon bark (*Cinnamon* sp) which has an absorbance at 280 nm at between about 15 to 20 O.D. per mg. cm, as shown in FIG. 12(*d*), and which additionally has the above mentioned chemical properties. In one embodiment, the extract has an absorbance at 280 nm at about 15 OD.

The present invention further concerns a CE obtainable by the following process:
  (i) grounding cinnamon bark into powder and stirring it into an aqueous buffer to obtain a solution;
  (ii) centrifuging the solution and separating a supernatant
  (iii) introducing a salt to obtain a precipitate.

The process may further comprise of the following steps:
  (iv) dissolving the precipitate obtained in step (iii) above in water or buffer at an essentially neutral pH;
  (v) separating the solution on a sepharose or Sephadex column; and
  (vi) eluting the solution with suitable buffer and varying concentrations of saccharide, preferably galactose to obtain the antiviral fractions of *cinnamon* sp.

By a preferred embodiment, the present invention concerns a CE obtained by the above process, wherein said salt used to obtain a precipitate is a chloride salt.

By another preferred embodiment, the present invention concerns an extract from cinnamon bark, (*Cinnamon* sp.) obtained by the following method:
  (i) grounding the bark into powder;
  (ii) stirring the bark in aqueous phosphate buffer 0.01M or 0.02M, pH 7.0;
  (iii) separating the supernatant by centrifugation to be used as the crude neutralizing extract;
  (iv) precipitate the active ingredient in the crude extract by 0.15M KCl or 0.08M $MgCl_2$;
  (v) dissolving the precipitate in water or 0.01M phosphate buffer at pH 7.0;
  (vi) loading the solution onto a column of sepharose 4B followed by a stepwise elution with phosphate buffer and various concentrations of galactose; and
  (vii) eluting the active antiviral material from the column by 0.15M galactose (FIGS. 12 *a, b, c*; fraction b or II).

The present invention also concerns compositions, which may be nutraceutical or pharmaceutical compositions, comprising the CE of the invention together with a pharmaceutically or nutraceutically acceptable carrier. The composition may be in a liquid, solid or semi solid state.

Furthermore, the present invention concerns a pharmaceutical composition or a nutraceutical composition for the treatment of an infection comprising as an active ingredient an effective amount of the CE together with a carrier suitable for pharmaceutical or nutraceutical compositions.

The term "treatment" in the context of the invention refers generally to one of the following: treatment of an established infection to cure it or decrease the viral load, decrease of at least one of the undesirable side effects of a viral disease, shorting the acute phase of the infection, and prevention of an infection before it occurs.

The term "influenza" or "Parainfluenza virus" or "HSV-1 virus" in accordance with a preferred embodiment of the invention refers to all known and newly evolving strains of these viruses, including animal viruses such as avian influenza.

The present invention further concerns a method for the treatment of a subject suffering from viral infection comprising administering to the subject in need of such treatment an effective amount of the extract as described above.

The viral infection is preferably an enveloped virus infection; more preferably a virus of the family Orthomyxoviruses, Paramyxoviruses, Herpesviruses, Retroviruses, Coronaviruses, Hepadnaviruses, Poxviruses, Togaviruses, Flaviviruses, Filoviruses, Rhabdoviruses, or Bunyaviruses.

Most preferably the virus infection is caused by a virus selected from: the avian influenza virus, Influenza virus, Parainfluenza virus (also referred to herein as "the Sendai virus"), NDV virus, HIV viruses or HSV-1 virus.

The subject in need may be a subject already suffering from an established viral infection, thus treatment is provided in order to cure the infection, decrease at least one undesired side effect of the infection or decrease in the duration of the infection, or a subject which is treated in a prophylactic manner in order to avoid subsequent infection by the virus.

The "subject" in accordance with the invention may be a human or an animal subject, and may be mammal or poultry especially farm and pet animals. The subject may also be fish in various aquacultures, bees and other insects of interest in agriculture.

Administration may be by any manner known in the art such as orally, parenterally, rectally, topically, nasally, by application to the eye, ear, nose or mucosal tissue, and the like. Preferably the administration is subcutaneously, intramuscularly, orally or intranasal.

The present invention further concerns a method for disinfecting an area suspected of being contaminated with viruses, comprising applying, for example by spraying, by brush or sponge application, etc., onto a suspected area an affective amount of the extract of the present invention. The surface may be any area in the house or in a medical facility that should be disinfected.

The disinfectant composition may be used to clean and disinfect surfaces such as ceramic tiles, PVC, porcelain, stainless steel, marble, silver and chrome to remove grease, wax, oil, dry paint and mildew and the like. The disinfectant composition may also be used as a laundry additive and may take the form of an aerosol spray, in which case, the composition is mixed with an appropriate propellant such as mist activators and sealed in an aerosol container under pressure.

In one specific embodiment, the composition is absorbed in a towel or a cloth, thus providing a disinfectant towel that may be used as means of applying the composition to the various surfaces or may be used to disinfect the hands and skin of an individual.

By another option the disinfectant composition may be applied onto plants for preventing or treatment plants viral infection. The plants may be, for example, fruit groves, vines, cotton fields, forests, prairies, private or public gardens, grass fields, vegetable fields and the like. The extract may also be used in a pre- or post-harvesting method of treating fruits and vegetables which may have been infected by viruses.

The disinfectant composition of the present invention may generally also include surfactants which are preferably selected from nonionic and cationic surfactants. The nonionic surfactant may, for example, be one or more selected from polyglycol ethers, polyalkylene glycol dialkyl ethers, and the addition products of alcohols with ethylene oxides and propylene oxides.

The cationic surfactant may be selected from various quaternary ammonium salts such as, but not limiting to octyl dimethyl benzyl ammonium chloride, octyl decyl dimethyl ammonium chloride, dioctyl dimethyl ammonium chloride, didecyl dimethyl ammonium chloride and dimethyl ethyl benzyl ammonium chloride, or mixtures thereof such as, but not limiting to, alkyl dimethyl benzyl ammonium chlorides and dialkyl dimethyl ammonium chlorides. In one embodiment, the composition may further comprise dyestuffs, perfumes, builders, chelating agents and corrosion inhibitors.

The composition comprising the extract of the present invention may also be used for the treatment of water reservoirs such as, but not limiting to, water systems, cooling systems, swimming pools, natural and artificial water reservoirs, fisheries, water tanks, aquariums, and any other volume of water.

In one embodiment, the composition is added in a dry form to the water reservoir in an amount sufficient to control the growth of viruses. In another embodiment, the dry composition is added to a water reservoir after being dissolved in an appropriate vehicle.

In another aspect of the present invention there is provided a method for purifying circulating air in airplanes, hospitals, kindergartens, offices, homes etc. by passing the air through appropriate filters containing or absorbed with the extracts of the invention. Within the scope of the present invention, also provided is a filter containing or absorbed with the CE of the invention. Such filter may be manufactured from any material suitable for the specific utility as known to a person skilled in the art. The filter may be a single unit filter or a multi-filter system and may be manufactured as to be adaptable to any existing purification unit, filtering or air-conditioning systems such as those found in clean-rooms, industry, hospitals, homes, offices and other facilities.

The extract of the present invention may be absorbed onto the filter during production of the filter or immediately prior to its use by methods known in the art such as: spraying of the extract onto of the filter at a predetermined flow and concentration, thereafter allowing the carrier to dry; dropping the filter into a solution of the extract for a period of time suitable for the extract to be absorbed onto the surface of the filter, thereafter allowing the solvent to dry; and the like.

All compositions of the present invention may be in a liquid or solid form depending on the specific utility.

By another aspect, the present invention concerns a method for producing a neutralized virus comprising contacting native viruses with an effective amount of the extract of the invention. The neutralized native viruses may be used for subsequent immunization against the viral infection instead of inactivated virus particles used today. Especially the use is for inactivated influenza, Parainfluenza viruses or HSV-1, that can be neutralized to produce a vaccine instead of the formalin inactivated viruses currently used. Thus, there is provided a method of immunization against a viral infection comprising administering to a subject the neutralized virus of the present invention.

The vaccine may be administered by various routes such as oral, intranasal, subcutaneous, intramuscular and others known to a person skilled in the art.

BRIEF DESCRIPTION OF THE DRAWINGS

In order to understand the invention and to see how it may be carried out in practice, some preferred embodiments will now be described, by way of non-limiting examples only, with reference to the accompanying drawings, in which:

FIG. 3 shows the inhibition of Influenza A PR8 by varying concentrations and different fractions of the crude extract of the invention;

DETAILED DESCRIPTION OF THE INVENTION a. Preparation of Active Extract

The active material was isolated by three steps as follows: a) the bark was purchased in the market and was ground into powder before it was stirred in aqueous phosphate buffer 0.01M-0.02M, pH 7.0, overnight. The supernatant was separated by centrifugation and was used as the crude neutralizing extract; b) The active material in the crude extract was precipitated by KCl 0.15M or 0.08M MgCl2, and the precipitate was dissolved in water or 0.01M phosphate buffer, pH 7.0 (CE ppt.); c) This solution was submitted onto column of sepharose 4B followed by a stepwise elution with phosphate buffer and various concentrations of galactose. The active antiviral material was eluted from the column by 0.15M galactose (FIGS. 12 a,b,c, fraction b or II).

B. Determination of Hemagglutinating Unit (HAU) and Hemolytic Activity

Hemagglutinating unit (HAU) was determined by using 0.4% washed human red blood cells. Viral hemolytic activity was tested in vitro in two successive steps: 1) attachment of the free virus onto 1 ml of 4% washed human erythrocytes for 15 minutes at room temperature; 2) incubation of the infected cells in 37° C. for 3 hours followed by centrifugation. The hemolytic activity of the viruses was determined by measuring the absorbance of the supernatant at 540 nm.

C. Elution of Active Fractions 60 ml of crude extract were precipitated by $MgCl_2$ 0.08M or KCl 0.15M. The precipitate was dissolved in water or in 0.01M phosphate buffer and was submitted on 10 ml column of sepharose 4B pre-washed with phosphate buffer 0.01M, pH 7.0. After submission, the column was washed with the buffer followed by stepwise elution of galactose 0.15M, 0.3M, and various concentrations of acetonitrile, as shown in FIGS. 12 a,b,c. The antiviral material was found in fraction b eluted from the column by 0.15M galactose (FIG. 12(c)) or fraction II in FIG. 12a, b.

EXAMPLE 1

Figure 1A:
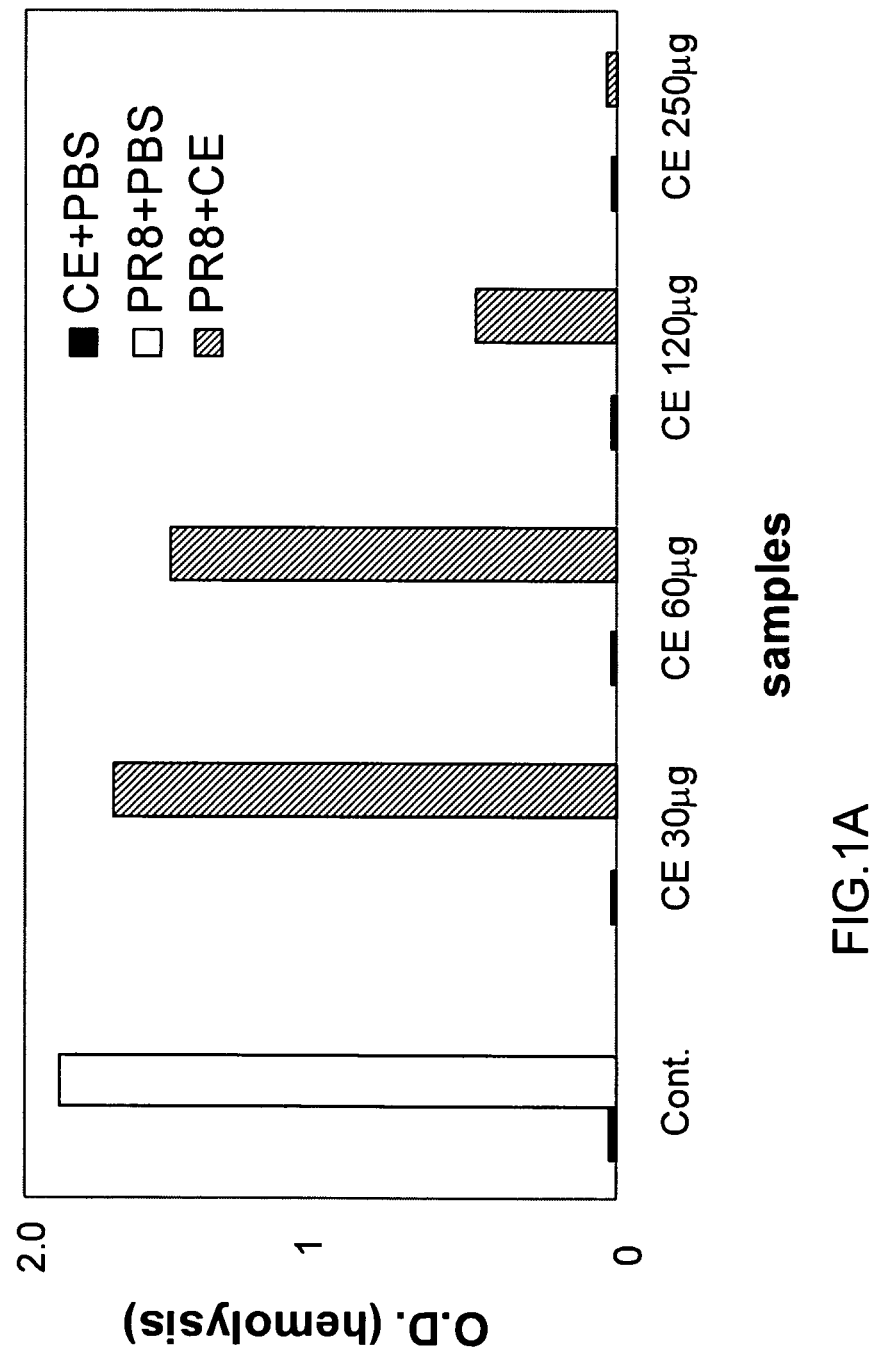
FIG. 1(a) shows the in vitro effect of varying concentrations of crude extract of the invention on the hemolytic activity of Influenza A.

In Vitro Inhibition of Hemolytic Activity by Influenza A by Crude Extract of the Invention Various amounts of crude extract were incubated with 256 HAU samples of Influenza A PR8 virus to test the inhibitory effect on the hemolytic activity of the virus, as described in the experimental procedure. Virus alone or the crude extract alone was used as controls. The results are shown in FIG. 1(a). The hemolytic activity of the virus was totally inhibited by 250 μg of the crude extract.

EXAMPLE 2

Figure 1B:
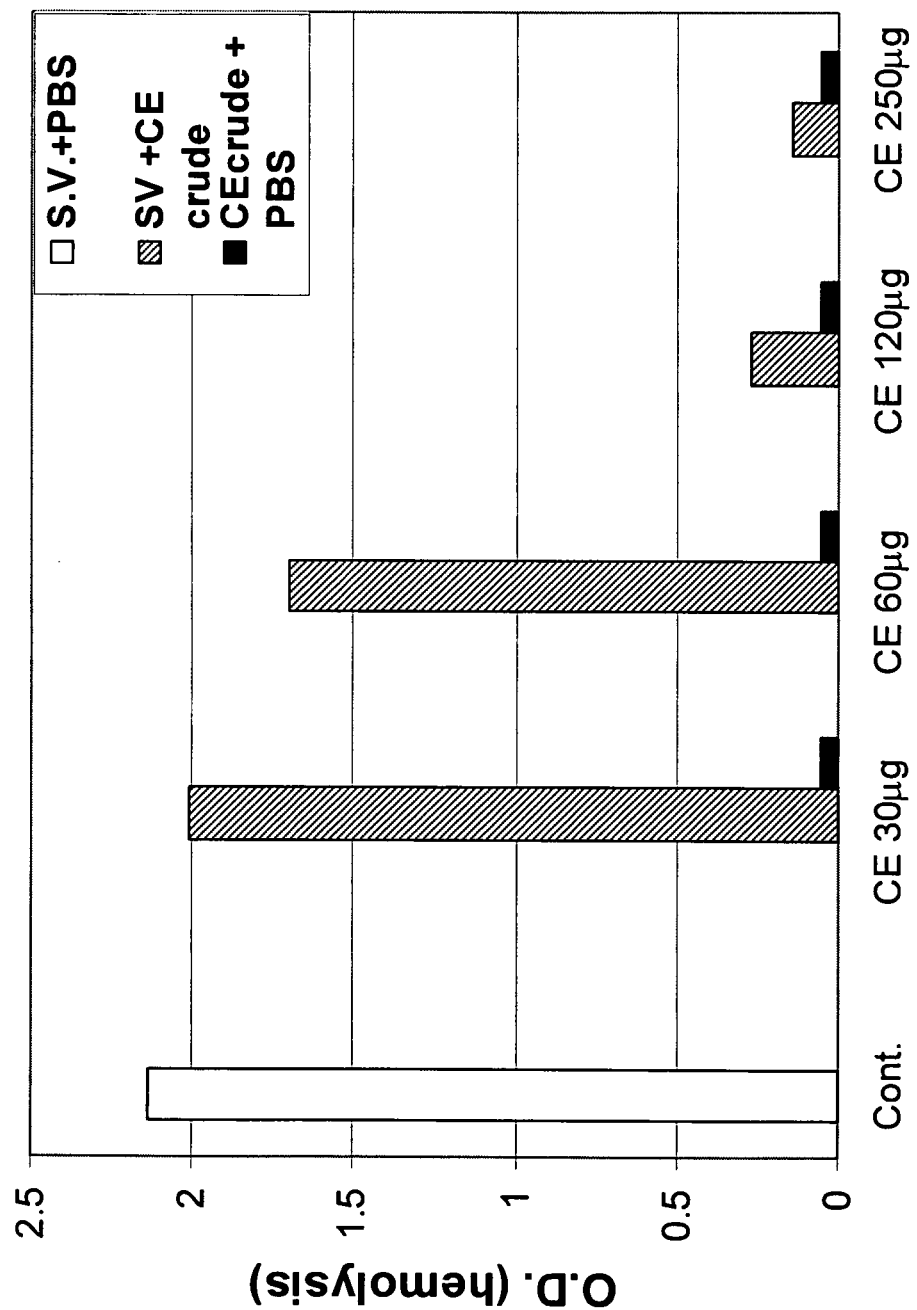
FIG. 1(b) shows the in vitro effect of varying concentrations of crude extract of the invention on the hemolytic activity of Parainfluenza (Sendai)

In Vitro Inhibition of Hemolytic Activity of Sendai Virus by the Extract of the Invention Various amounts of crude extract were incubated with 256 HAU samples of Sendai virus to test the inhibitory effect on the hemolytic activity of the virus, as described in the experimental procedure. Virus alone or the crude extract alone was used as controls. The results are shown in FIG. 1(b). The hemolytic activity of the virus was totally inhibited by 250 μg of the crude extract.

EXAMPLE 3

Figure 2:
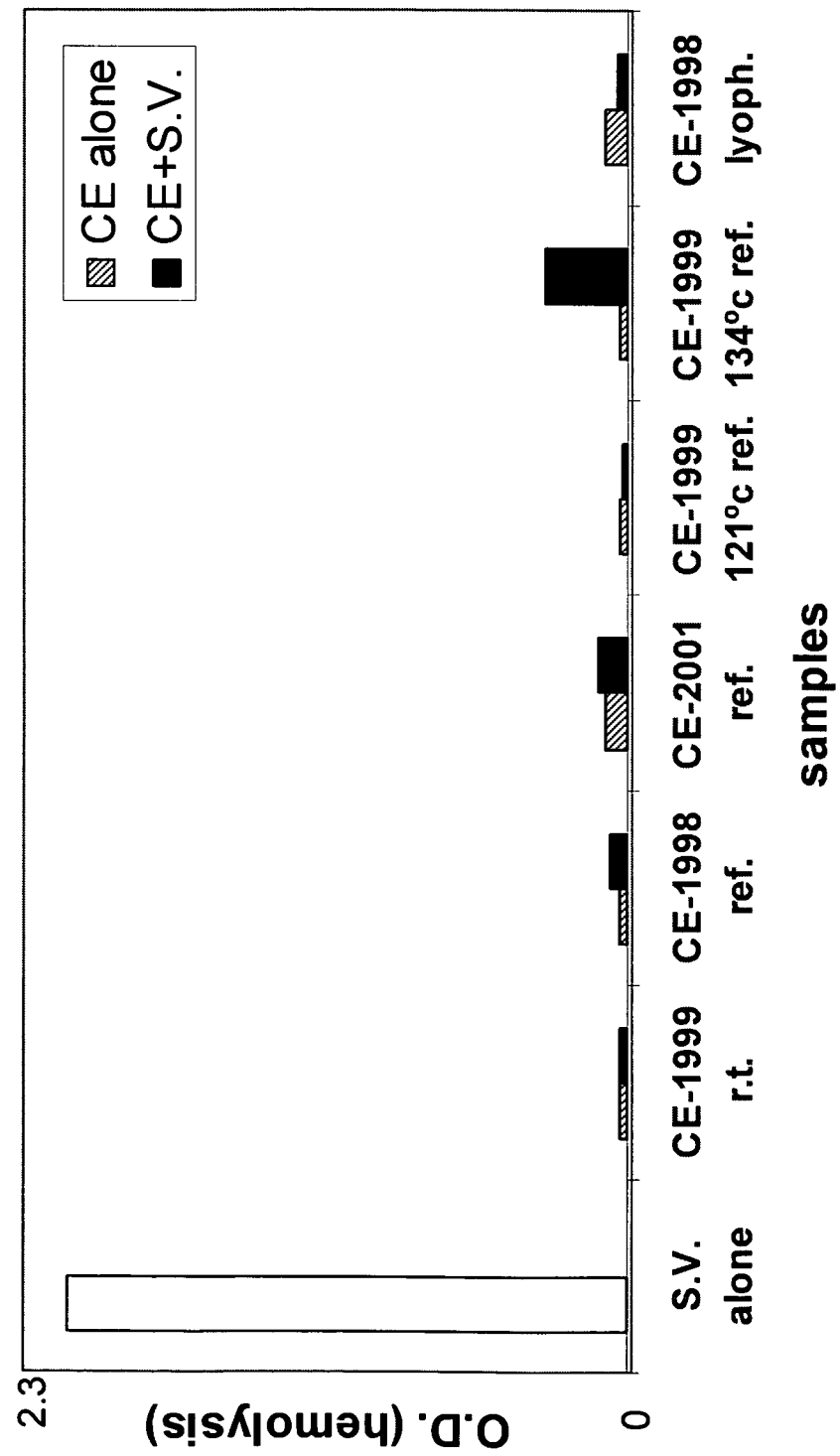
FIG. 2 shows the antiviral effect of extracts treated by autoclaving or after 4 years maintenance.

Maintenance of Antiviral Activity after Time Period, Refrigeration and Autoclave The cinnamon extracts (CE) or autoclaved CE was kept at room temperature or in the refrigerator for 4 years before testing their ability to inhibit the hemolytic activity of Sendai Virus (S.V.). 200 μg of CE were mixed with 256 HAU of the virus and hemolysis was tested as described in the experimental procedures. The results are shown in FIG. 2. As can be seen, the antiviral activity of CE was maintained after all treatments although it lost some activity after autoclaving at 134° C.

EXAMPLE 4

Inhibition of Influenza A PR8 by Various Fractions of the Extract of the Invention, Treated with Various Reagents Autoclaved CE fractions were incubated with 256 HAU of Influenza A PR8 virus at room temperature for 15 minutes. After application on human erythrocytes, the mixture was transferred to 37° C. for 3 hours. The results are shown in FIG. 3. 50-100 μg of each CE fractions was sufficient to inhibit the viral hemolytic activity. CE ppt (isolated fraction obtained by salting out with KCl 0.15M) expressed the strongest antiviral activity.

Figure 4A:
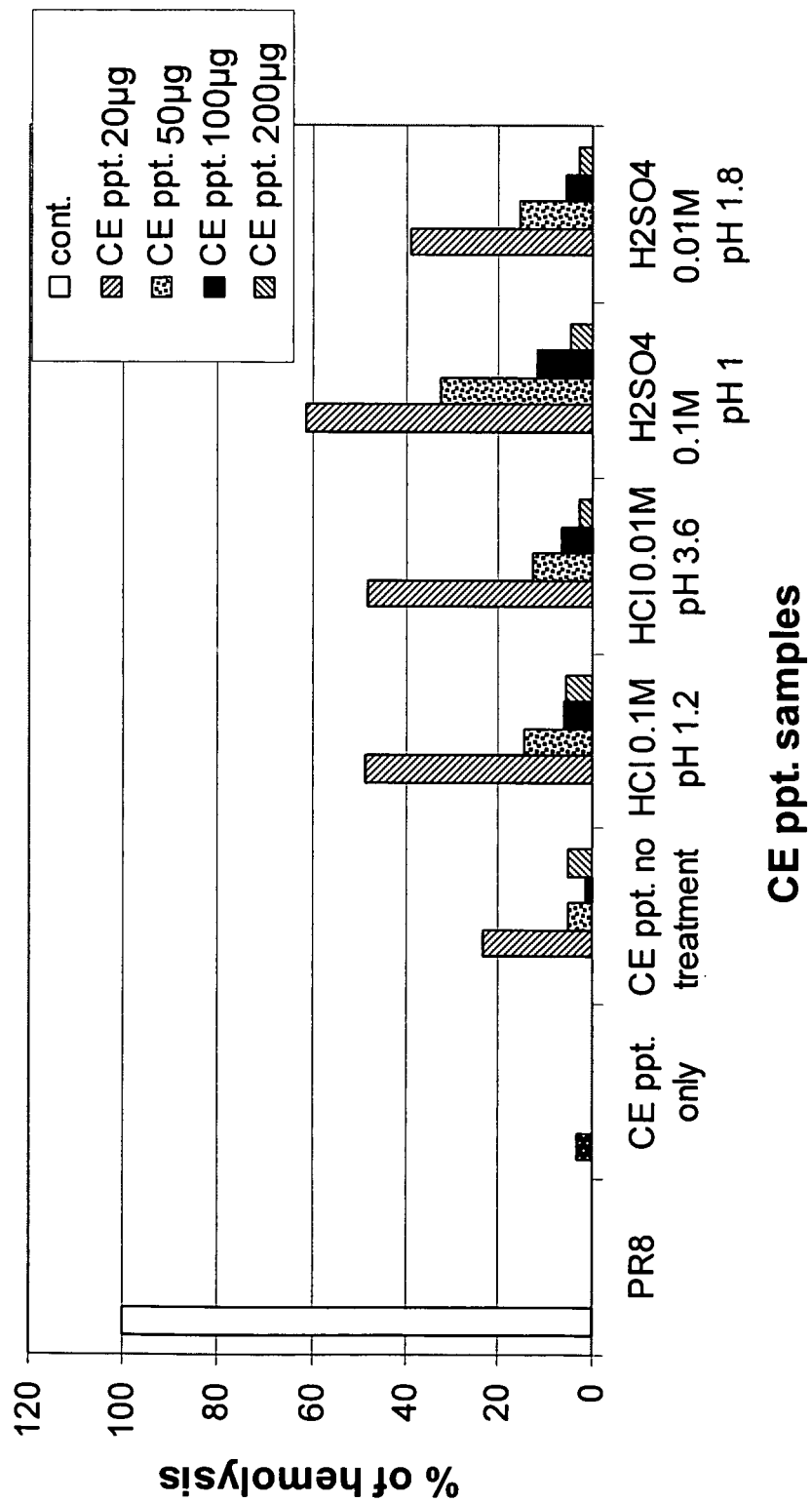
FIG. 4(a) shows the antiviral effect of a fraction of the extract treated with HCl and $H_2SO_4$.

CE ppt was incubated with 0.01M or 0.1M HCl and $H_2SO_4$ at room temperature for 3 hours followed by neutralization to pH 7 before examining its ability to neutralize the virus, as described in FIG. 3. The results after this treatment are shown in FIG. 4(a).

Figure 4B:
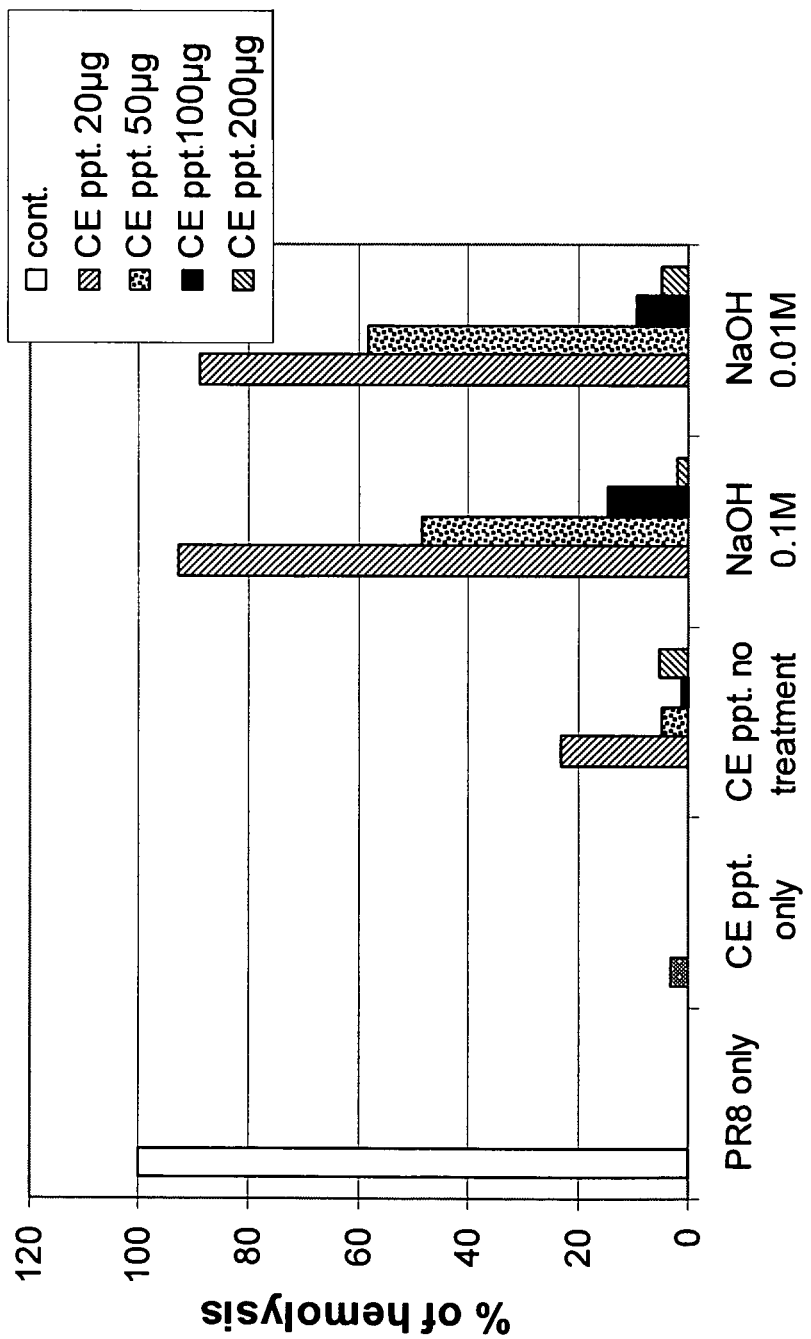
FIG. 4(b) shows the antiviral effect of a fraction of the extract treated with NaOH.

CE ppt was incubated with 0.01M or 0.1M NaOH at room temperature for 3 hours, followed by neutralization to pH 7, before examining its ability to inhibit the hemolytic activity of the virus, as described in FIG. 3. The results are shown in FIG. 4(b). The treated material remained partially active. CE ppt is the precipitated fraction obtained by salting out with KCl 0.15M.

Figure 5:
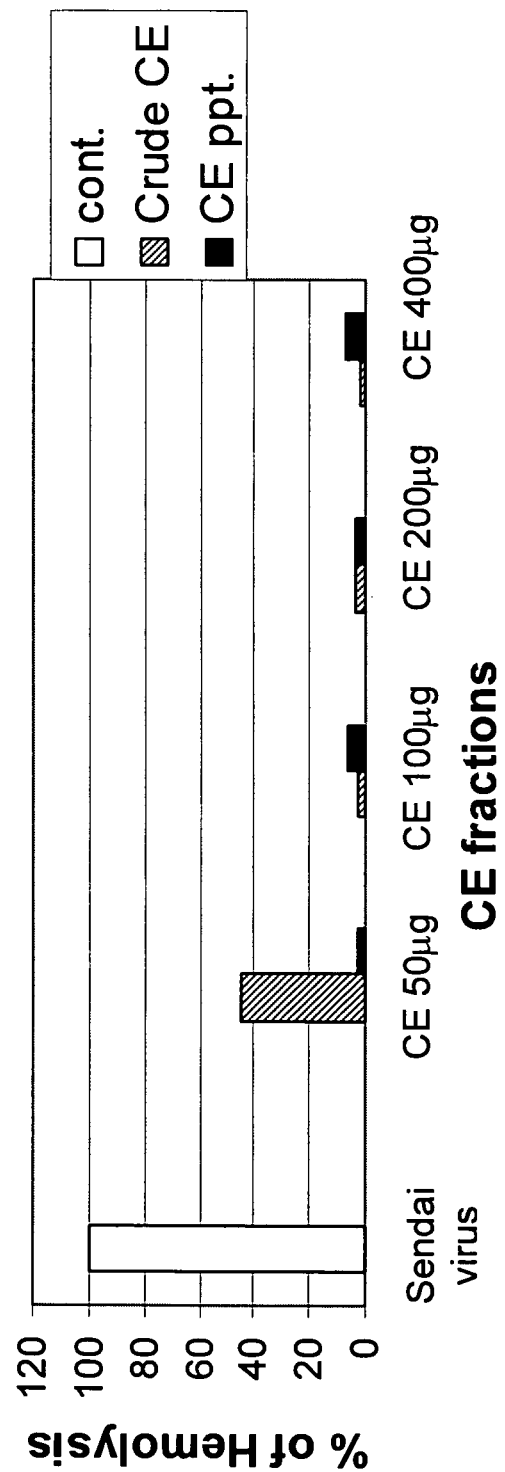
FIG. 5 shows the antiviral effect of a fraction extracted treated with dialysis against water.

CE fractions were dialyzed against water before examining the antiviral activity as described in FIG. 3. The results are shown in FIG. 5. The active material in the CE fractions has a molecular weight greater than 10 KDa (the dialysis bag cut-off).

EXAMPLE 5

Figure 6A:
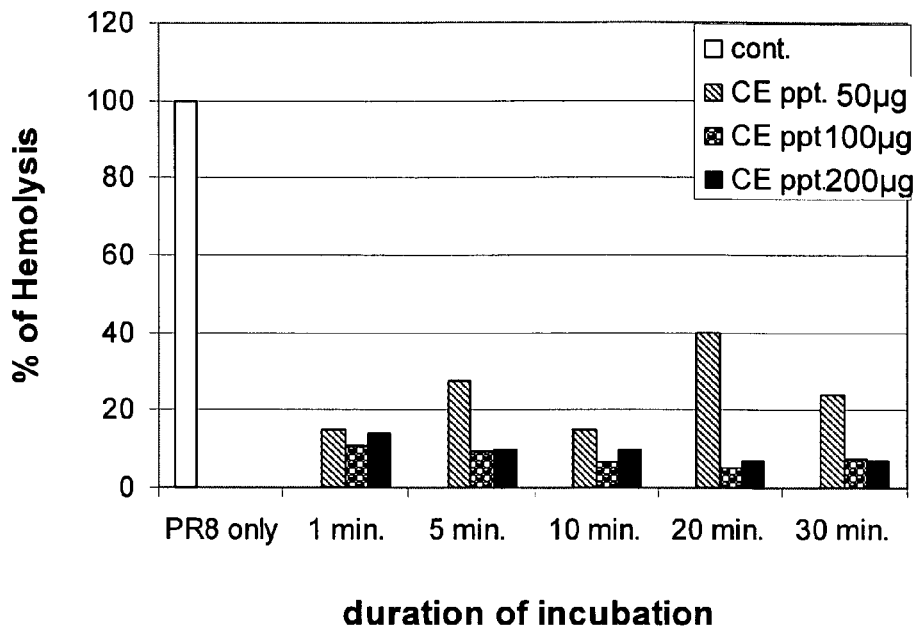
FIG. 6(a) shows the antiviral effect of the extract on Influenza A-PR8 after varying incubation periods.

Inhibition of Influenza A PR8 by the Extract of the Invention after Incubation for Various Time Periods 50-200 μg samples of the CE ppt fraction were incubated with the virus for 1-30 minutes at room temperature, before adding the erythrocytes. Hemolytic activity of the virus was determined as described in FIG. 3. The results are shown in FIG. 6(a). Short incubation (one minute) was sufficient to neutralize the virus.

Figure 6B:
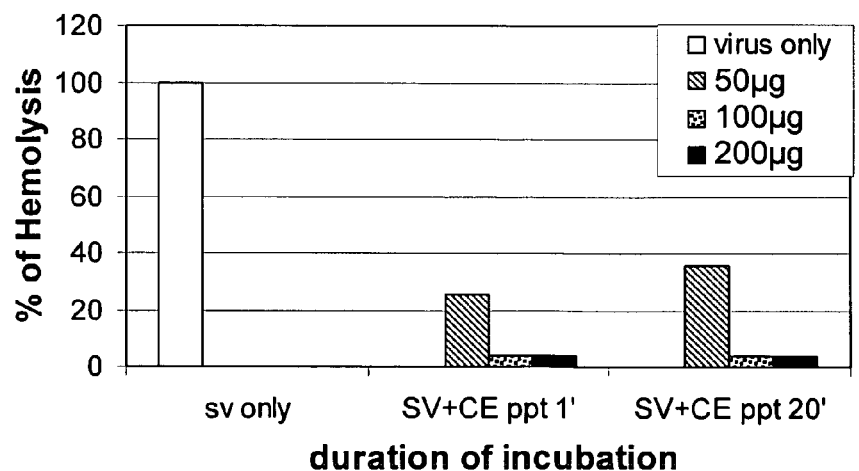
FIG. 6(b) shows the antiviral effect of the extract on Parainfluenza (Sendai) after varying incubation periods.

50-200 μg samples of the CE ppt fraction were incubated with the virus for 1 min. or 20 minutes at room temperature before adding the erythrocytes. Hemolytic activity of the virus was determined as described in FIG. 3. The results are shown in FIG. 6(b). Short incubation (one minute) was sufficient to neutralize the virus.

EXAMPLE 6

Inhibition of Influenza A PR8 Pre-Absorbed onto Erythrocytes

Figure 7:
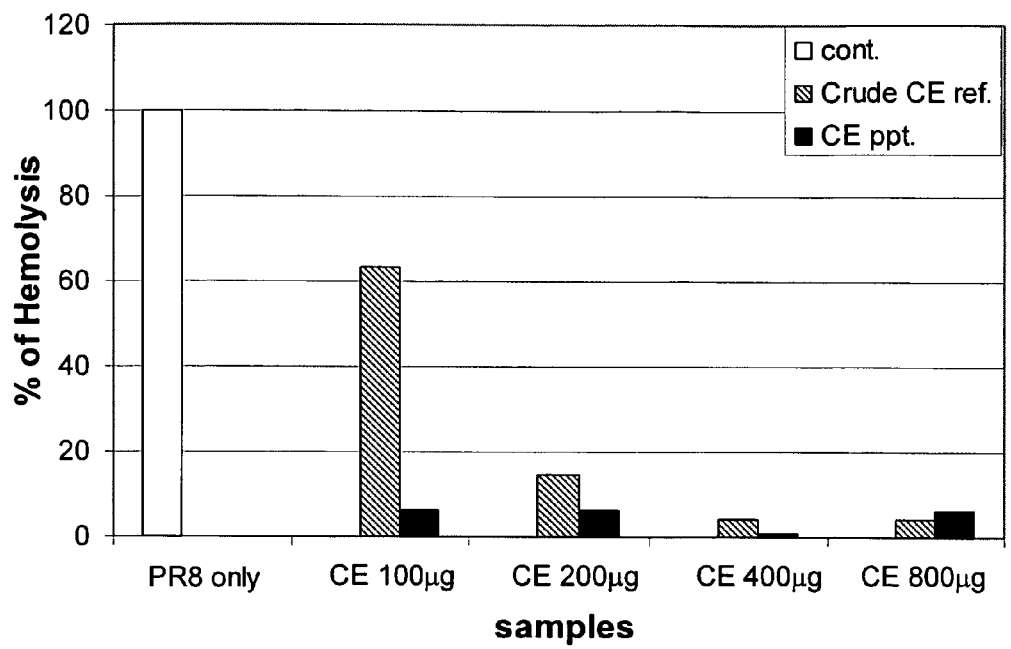
FIG. 7 shows inhibition of Influenza A PR8 pre-absorbed onto erythrocytes by varying concentrations of the extract of the invention.

256 HAU of Influenza A PR8 virus were absorbed to human erythrocytes at room temperature before application of various CE fractions, and incubation at 37° C. as described in methods. The results are shown in FIG. 7. Each of the CE fractions inhibited the hemolytic activity of the virus, although this required at least two-fold amount of each fraction compared to the direct interaction between the free virus and the CE fractions.

Figure 8:
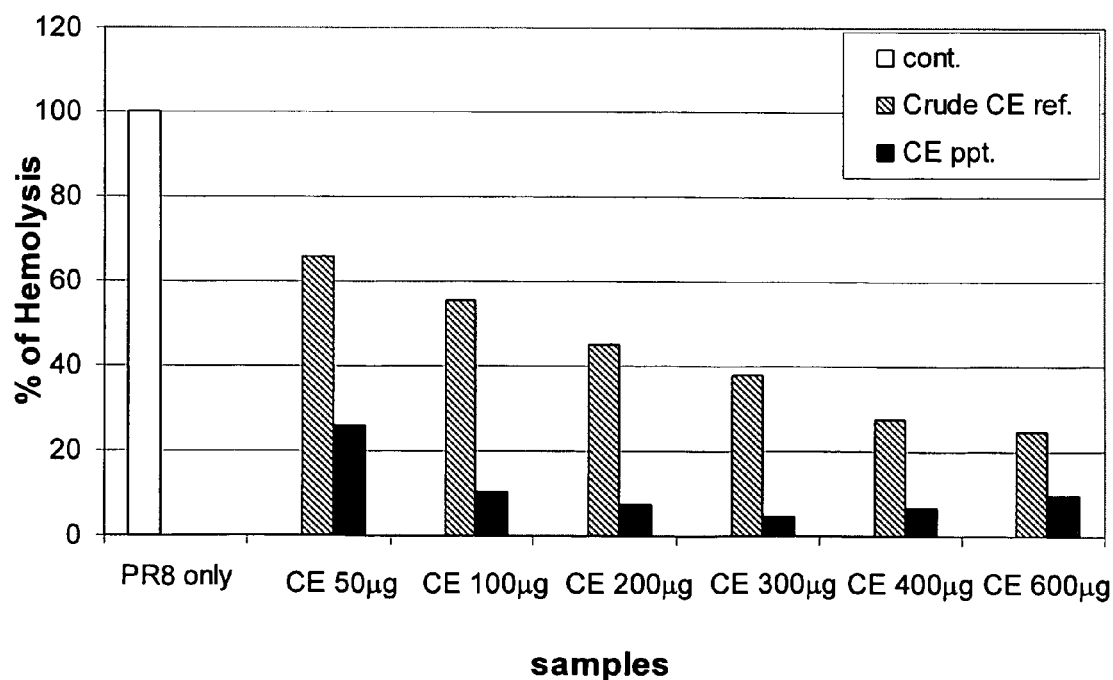
FIG. 8 shows protection against Influenza A PR8 after pre-absorption of CE fractions onto erthrocytes.

Two CE fractions were absorbed onto human erythrocytes, and the excess was washed twice with PBS before application of 256 HAU of Influenza A PR8 virus at room temperature and incubation at 37° C. as described in methods. The results are shown in FIG. 8. Both the refrigerated crude extract and the isolated fraction CE ppt protected the erythrocytes from the hemolytic activity of the virus, but CE ppt was more effective. The amount needed for the protections was 4-10 times higher than the amount that inhibited the virus by direct interaction.

EXAMPLE 7

Figure 9:
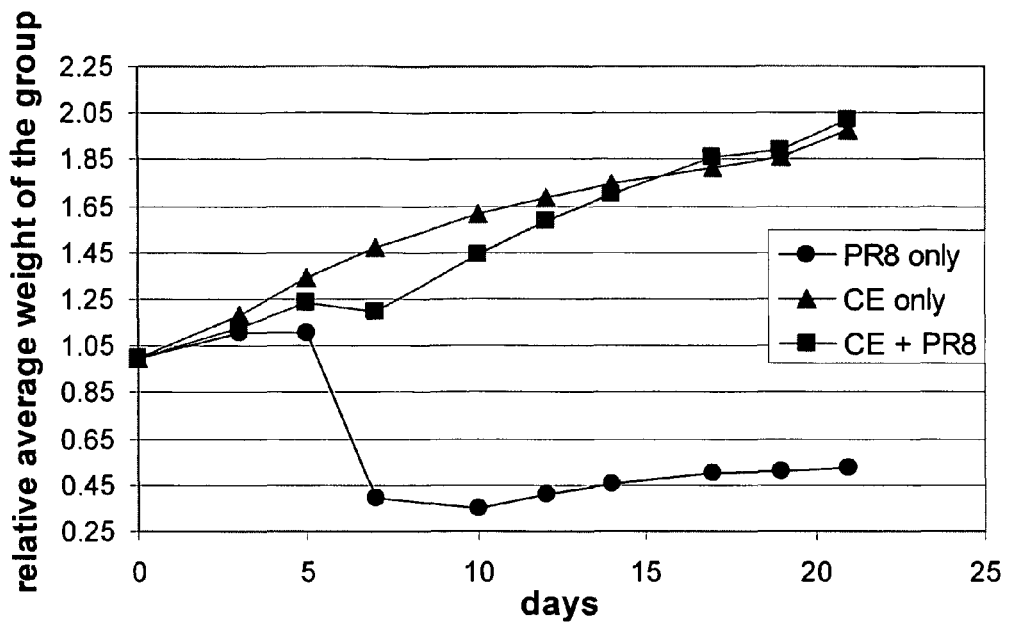
FIG. 9 shows in vivo results showing the effect of the extract of the invention on weight of mice infected with Influenza A virus.

In Vivo Effect of Treatment of the Extract of the Invention on Influenza A Infected Mice 3.5 week old mice were injected i.v. (caudal vein) with 250 µl of PBS containing 128 HAU of Influenza A virus alone or Influenza A mixed with 250 µg of the crude extract or the crude extract alone. The mice were weighed at 2-3 day intervals. The results are shown in FIG. 9. While the mice infected with the virus alone lost weight and most of them died within 7-10 days, the mice injected with a mixture of the virus and the crude extract continued to gain weight almost on a level with those injected with the crude extract alone. Each group included 10 mice.

EXAMPLE 8

Figure 10:
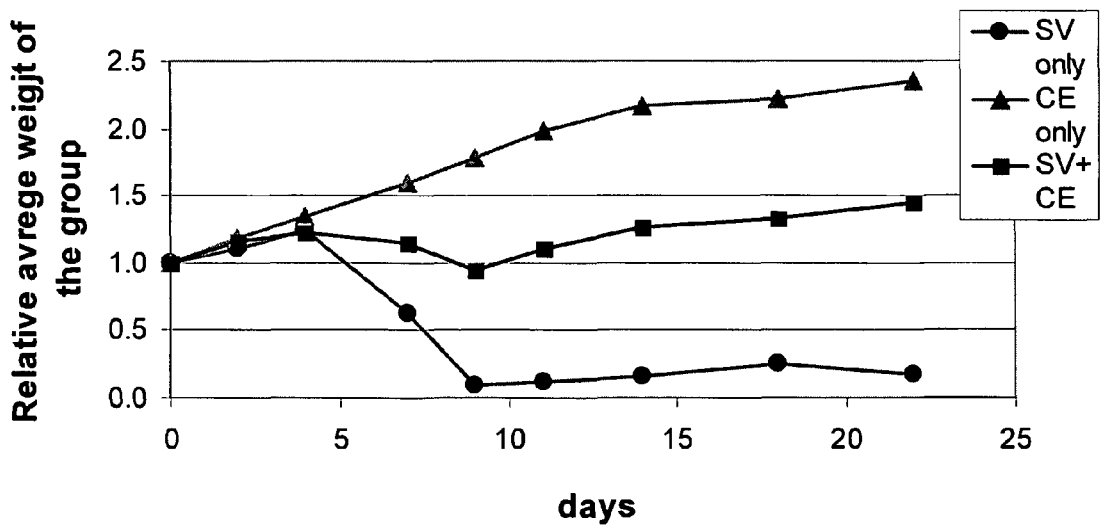
FIG. 10 shows in vivo results showing the effect of the extract of the invention on weight of mice infected with Parainfluenza Sendai virus.

In Vivo Effect of the Extract of the Invention on Sendai Virus 3.5 week old mice were allowed to inhale 50 µl of water containing 64 HAU of Sendai virus alone, or virus mixed with 125 µg of the crude extract, or the crude extract alone. The mice were weighed at 2-3 day intervals. The results are shown in FIG. 10. While the mice infected with the virus alone lost weight and most of them died within 7-10 days, the mice treated internasally with a mixture of the virus and the crude extract recovered and gained weight. Each group included 10 mice.

EXAMPLE 9

Figure 11A:
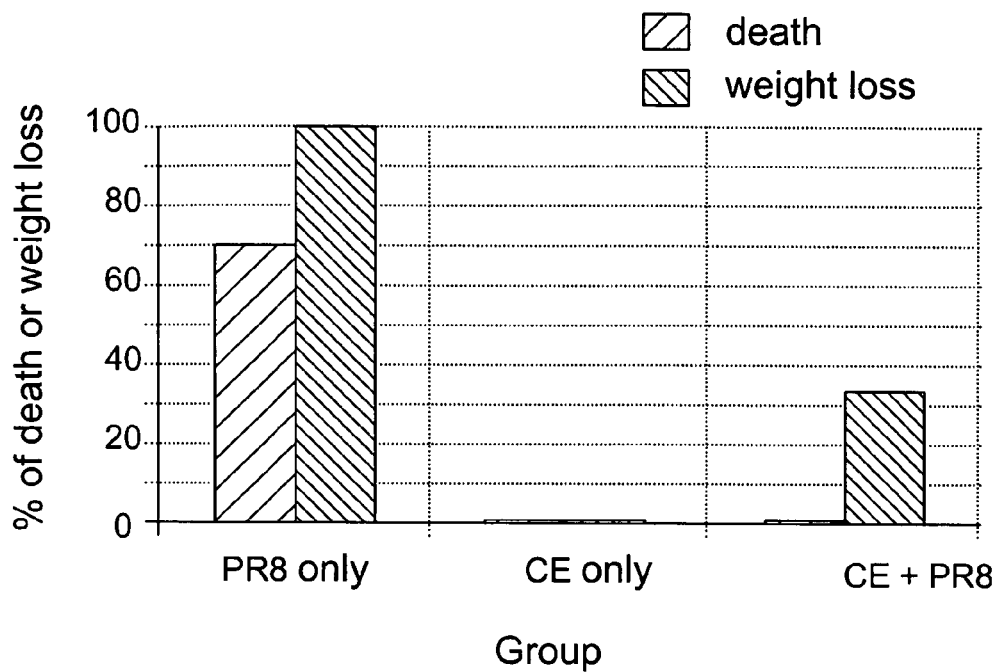
FIG. 11(a) and FIG. 11(b) show a histogram showing death and relative weight of mice infected with Influenza A PR8 virus incubated with the CE inhibitor.
Figure 11B:
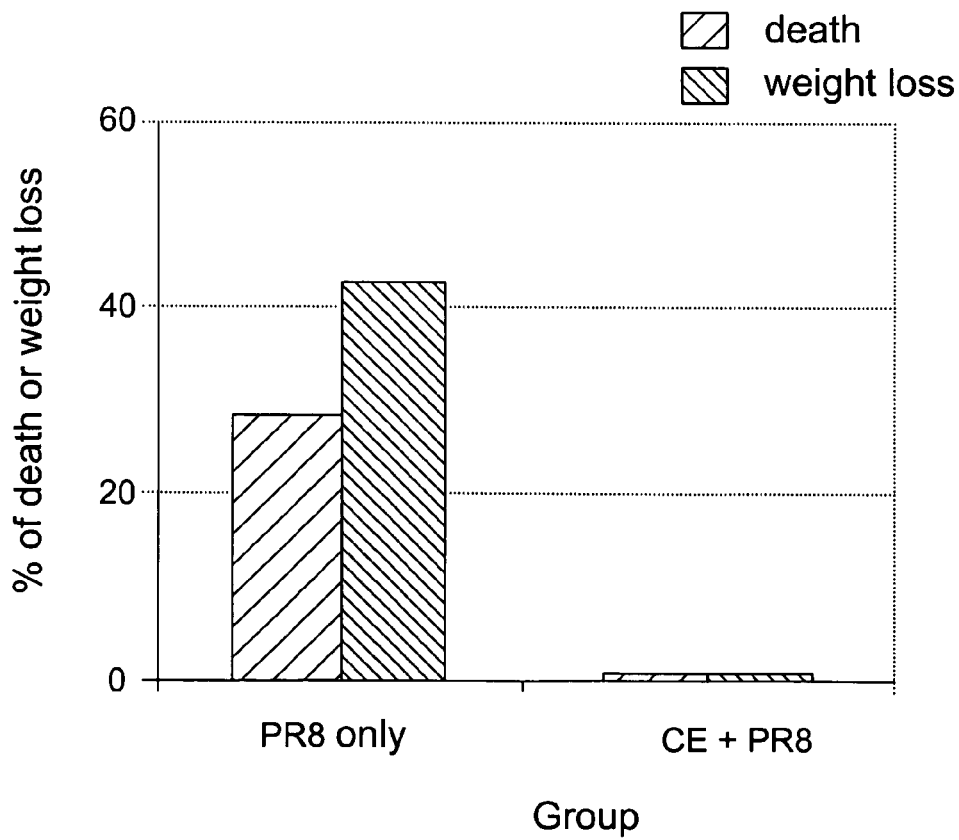
Figure 12A:
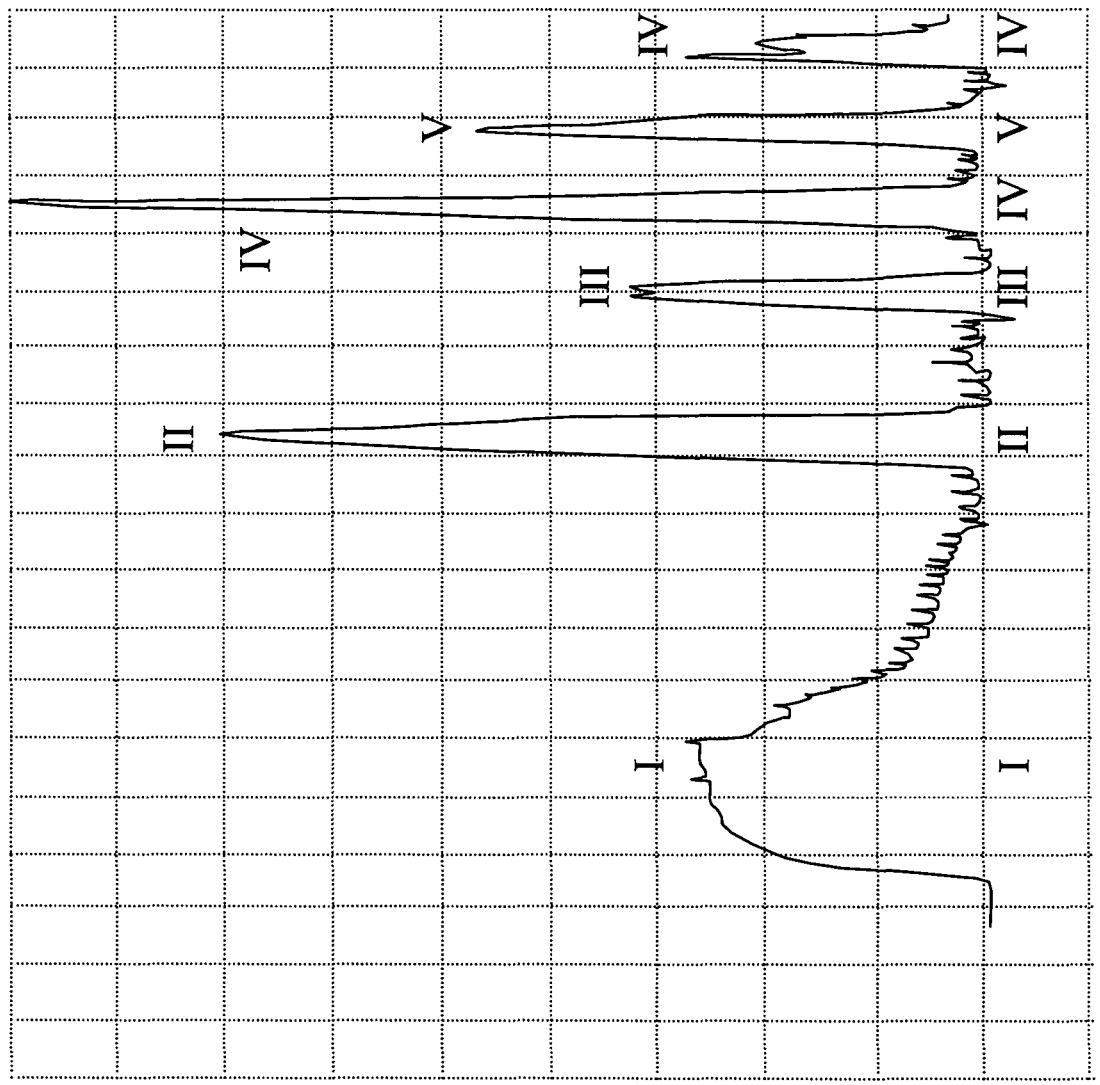
FIG. 12(a) shows galactose elution of fraction from sepharose 4B—fraction (II) having antiviral activity.
Figure 12B:
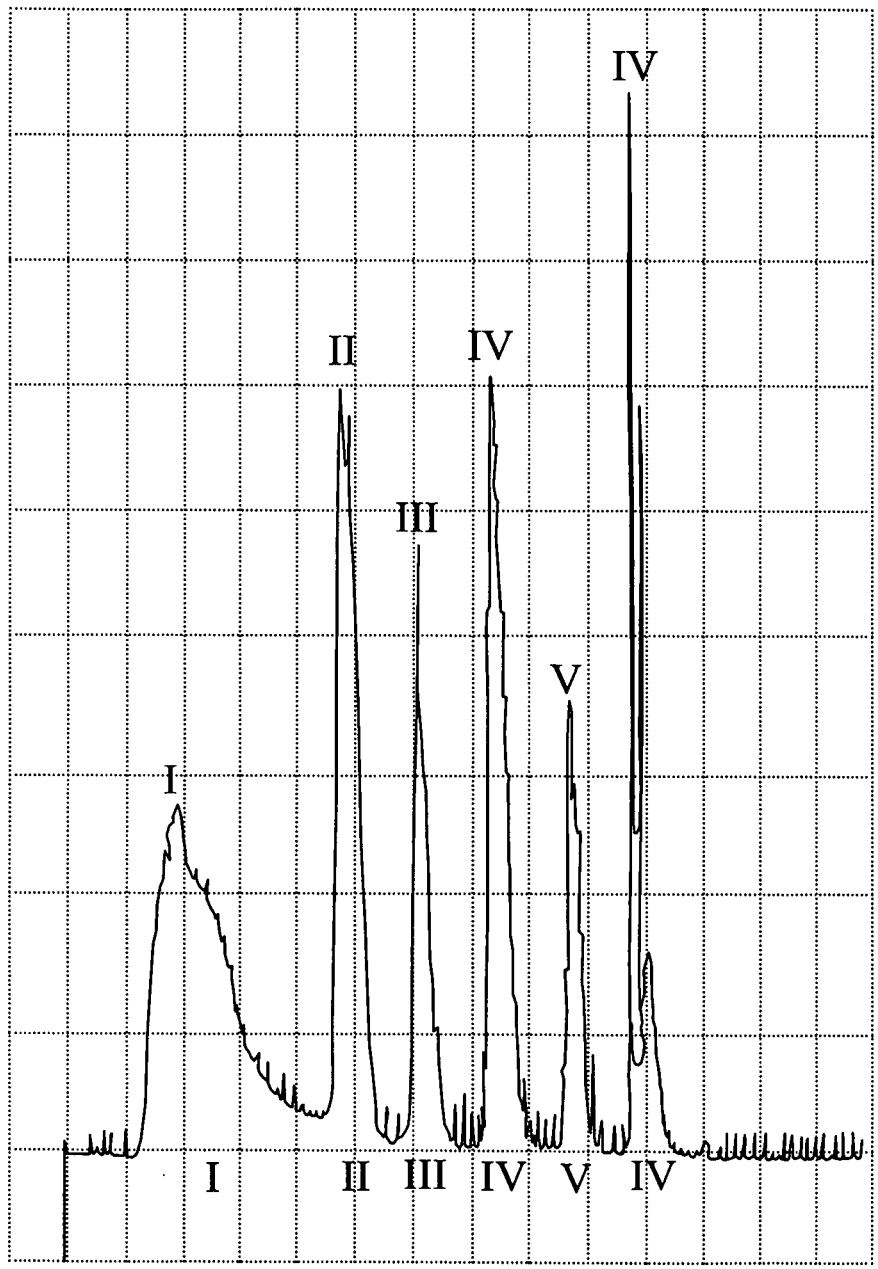
FIG. 12(b) shows galactose elution of fraction from sepharose 4B—Fraction (II) having antiviral activity.
Figure 12C:
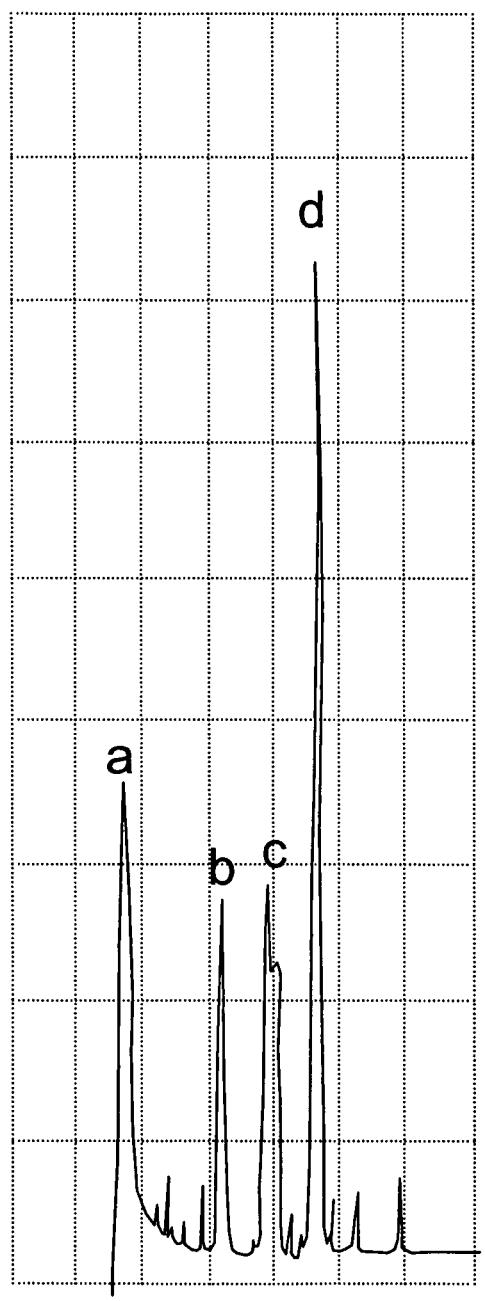
FIG. 12(c) shows galactose elution of fraction from sepharose 4B—Fraction (b) having antiviral activity.
Figure 12D:
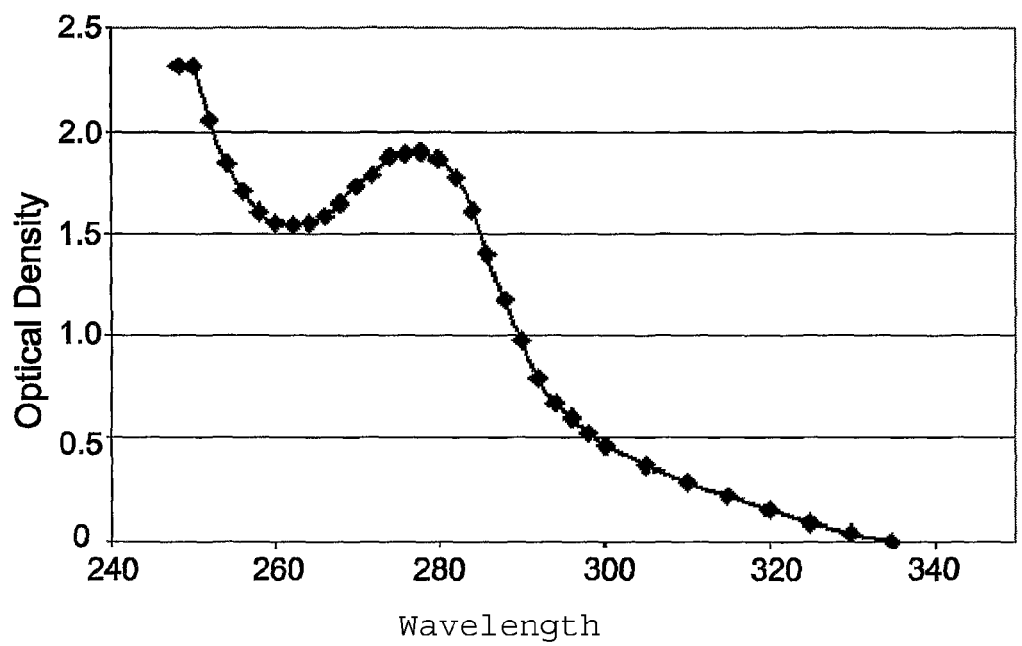
FIG. 12(d) shows the optical density curve of the cinnamon extract.

In Vivo Effect of the Extract of the Invention on Influenza A PR8 Infection 3.5 weeks old mice were injected into the caudal vein with 128 HAU of Influenza A PR8 pre-incubated with 250 µg of the CE inhibitor for 30 minutes at room temperature. The mice were weighed every 2-3 days for 3 weeks. The results are shown in FIGS. 11(a) and 11(b). Weight loss of over 2 gr. was marked as a weight loss event. No deaths occurred among the mice infected with the virus pre-incubated with the inhibitor. Each group included 10 mice.

EXAMPLE 10

Effect of the Extract of the Invention of HSV-1 Infected Vero Cells

100 PFU aliquots of HSV1 were mixed with 50 µg (B) of autoclaved CE ppt in 100 µl medium M-199 and immediately submitted on Vero cells in 24 wells plate. After 2 hours incubation at 37° C., 5% $CO_2$, each well was overlaid with additional one ml medium and the incubation continued 3 days. The cells were washed twice with PBS before fixation with methanol and staining with Giemsa.

Figure 13A:
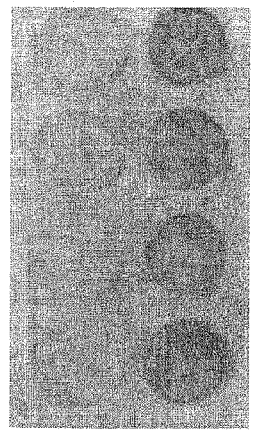
FIG. 13(a) shows the effect of the crude extract of the invention on HSV-1 infected Vero cells.

The results are shown in FIG. 13(a). As can be seen in lane (A), cells with HSV alone were detached and washed from plate. Against this, cells with HSV mixed with 50 µg CE ppt were not affected, indicating that the extracts of the invention protected the Vero cells from HSV-1 infection.

50 µg fixed aliquots of CE ppt were incubated with samples containing $10^2$-$10^6$ PFU of HSV1 for 1 hour in 100 µl of medium M-199. Each sample was applied on confluent Vero cell monolayer growth in 24 wells plate and the plate was incubated at 37° C., 5% $CO_2$ for 2 hours. One ml medium was added to each well and incubation continued 3 days. The cells were washed twice with PBS before fixation with methanol and staining with Giemsa.

Figure 13B:
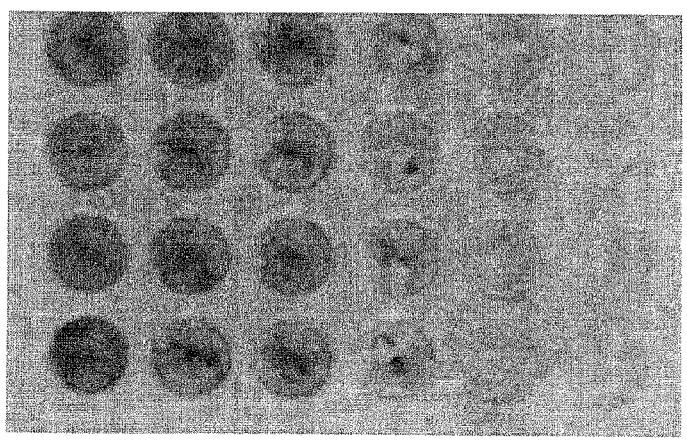
FIG. 13(b) shows the effect of varying concentrations of HSV-1 (on Vero cells) in response to a fixed amount of the extract of the invention.

Results are shown in FIG. 13(b). The lanes were as follows: A—$10^2$ PFU, B—$10^3$ PFU, C—$10^4$ PFU (A-C—virus was totally inhibited); D—$10^5$ PFU—Virus was partially inhibited; E—$10^6$ PFU—Virus was hardly inhibited; F—$10^2$ PFU of virus without inhibitor, cells were detached and washed from wells.

Aliquots containing $10^6$ PFU of HSV1 were mixed with 50 µg-400 µg of CE ppt in 100 µl medium M-199. Each mixture immediately submitted on confluent Vero cell monolayers in 24 cells plate. After 1 hour incubation at 37° C., 5% $CO_2$, the cells from each well were overlaid with one ml M-199 and the incubation continued 3 days. The cells were washed twice with PBS before fixation with methanol and staining with Giemsa.

Figure 13C:
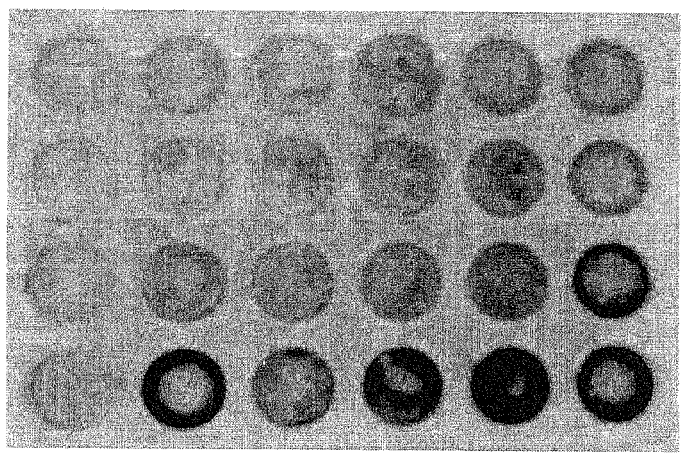
FIG. 13(c) shows the effect of increasing amounts of the compound of the invention on fixed amounts of HSV-1 Vero infected cells.

The results are shown in FIG. 13(c). The lanes were as follows: A—$10^6$ PFU of virus without inhibitor, cells were detached and washed from wells; B—F: $10^6$ PFU of virus with various amounts of CE ppt as follows: B—50 µg, C—100 µg, D—200 µg, E—300 µg, F—400 µg. There is direct correlation between inhibition and increasing amounts of the CE ppt.

As can be seen from all these results the extract of the invention was able to protect Vero cells from the damaging effects caused by HSV-1 infection.

EXAMPLE 11

Figure 14A:
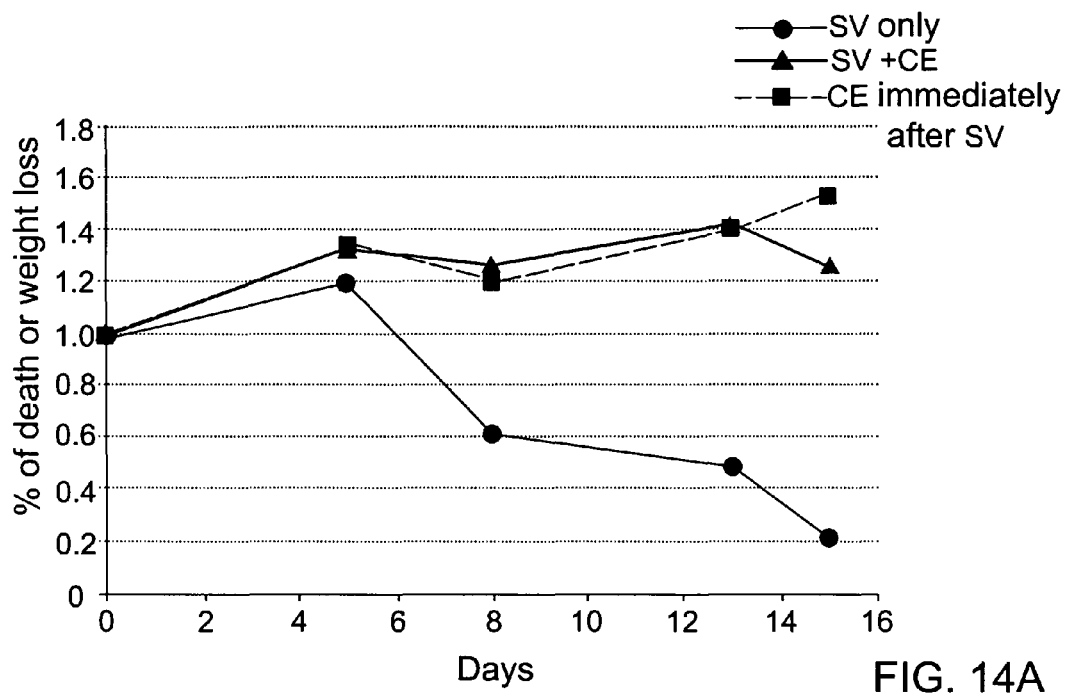
FIG. 14(a) depicts changes in weight after i.n. administration of the inhibitor after viral infection in mice.

Effects of the Extract of the Invention on the Weight Loss of Mice Infected with Virus Three and a half week old mice were infected with 32 HAU of Sendai virus which was pre-incubated for 20 minutes with 125 µg of the CE ppt inhibitor or treated with the CE ppt immediately after infection with the virus. The mice were then weighed every 2-3 days during a 3-week period. As FIG. 14a shows, the two groups of mice which had been treated with the inhibitor started to gain weight 8 days post infection (P=0.017). The control group which had not been treated with the inhibitor continued losing weight.

Figure 14B:
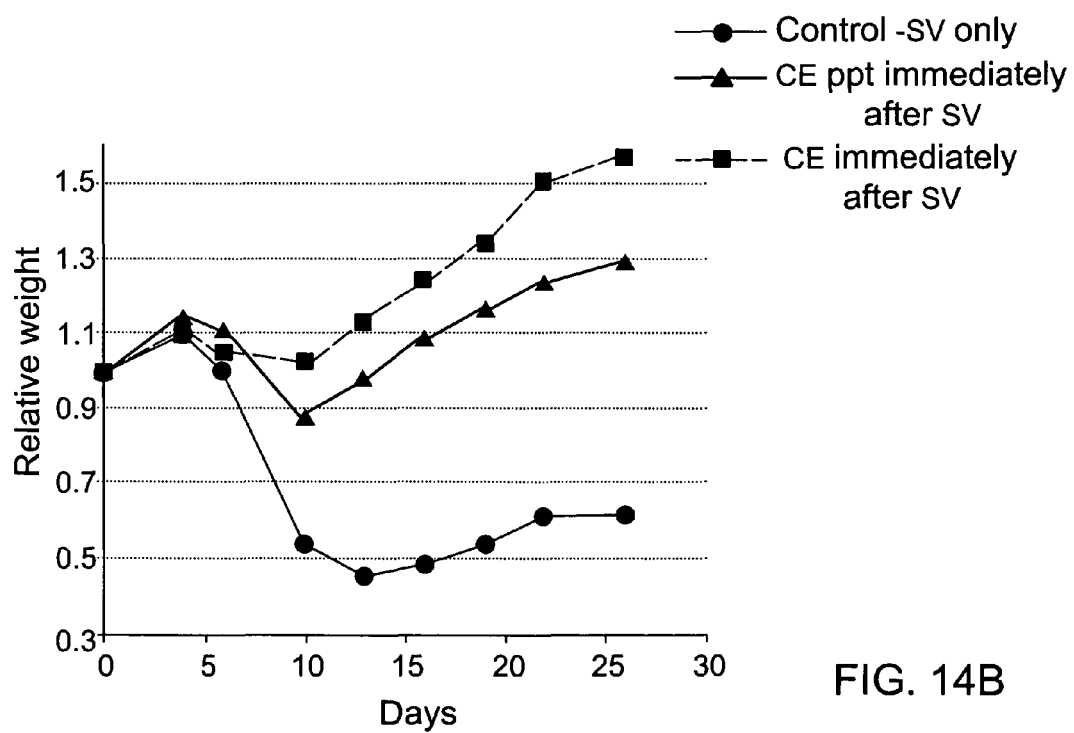
FIG. 14(b) depicts changes in weight after treatment with the inhibitor immediately or an hour after injection with the virus.

In a different experiment, 3.5-week old mice were infected internasally with 32 HAU of Sendai virus and immediately thereafter treated with 125 μg of the CE ppt inhibitor. A second group of mice was treated with the CE ppt inhibitor one hour post infection. The mice were weighed every 2-3 days for a period of 2.5 weeks. As FIG. 14b shows, Mice which had been treated with the CE ppt inhibitor continued to gain weight whereas mice in the control group lost weight significantly (P=<0.001).

EXAMPLE 12

Effect of the Extract of the Invention on the Weight Loss of Immunized Mice

Figure 14C:
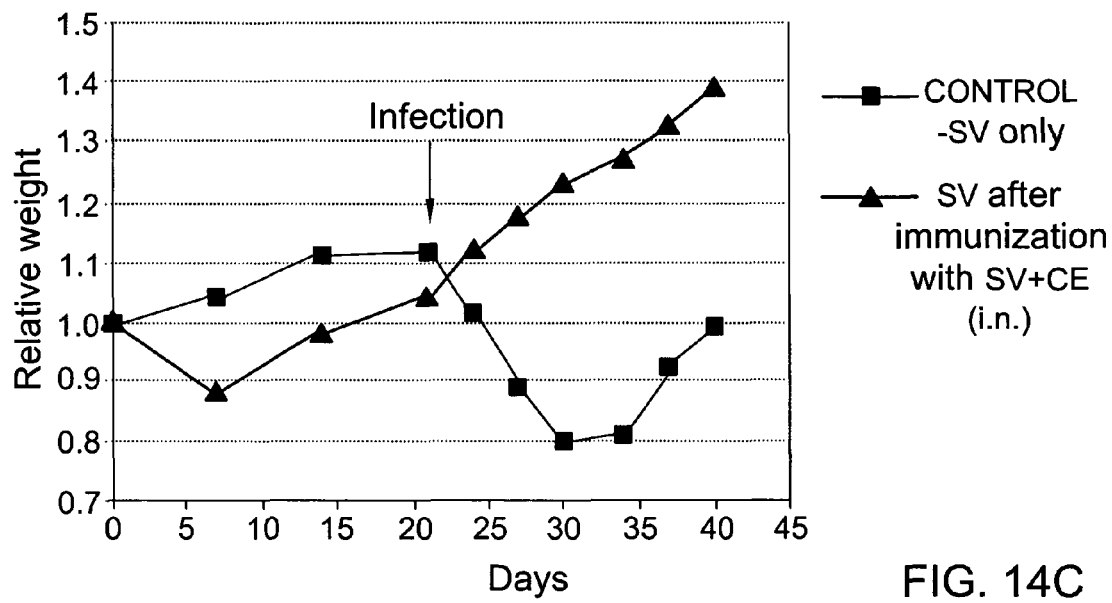
FIG. 14(c) depicts changes in weight of mice immunized i.n. by Sendai virus and the inhibitor before infecting the mice with naïve Sendai virus.

In another set of experiments, immunization with the CE ppt inhibitor was tested. 3.5 week old mice were immunized intranasally (i.n). with 32 HAU of Sendai virus mixed with 125 μg of the CE ppt. The controlled group received only water. Three weeks post immunization both groups of mice were infected with 64 HAU of the naïve virus alone. The mice were weighed every 2-3 days over a period of 40 days. As FIG. 14c shows, the immunized mice were not affected by the subsequent virus infection and kept gaining weight (P=0.013).

Figure 14D:
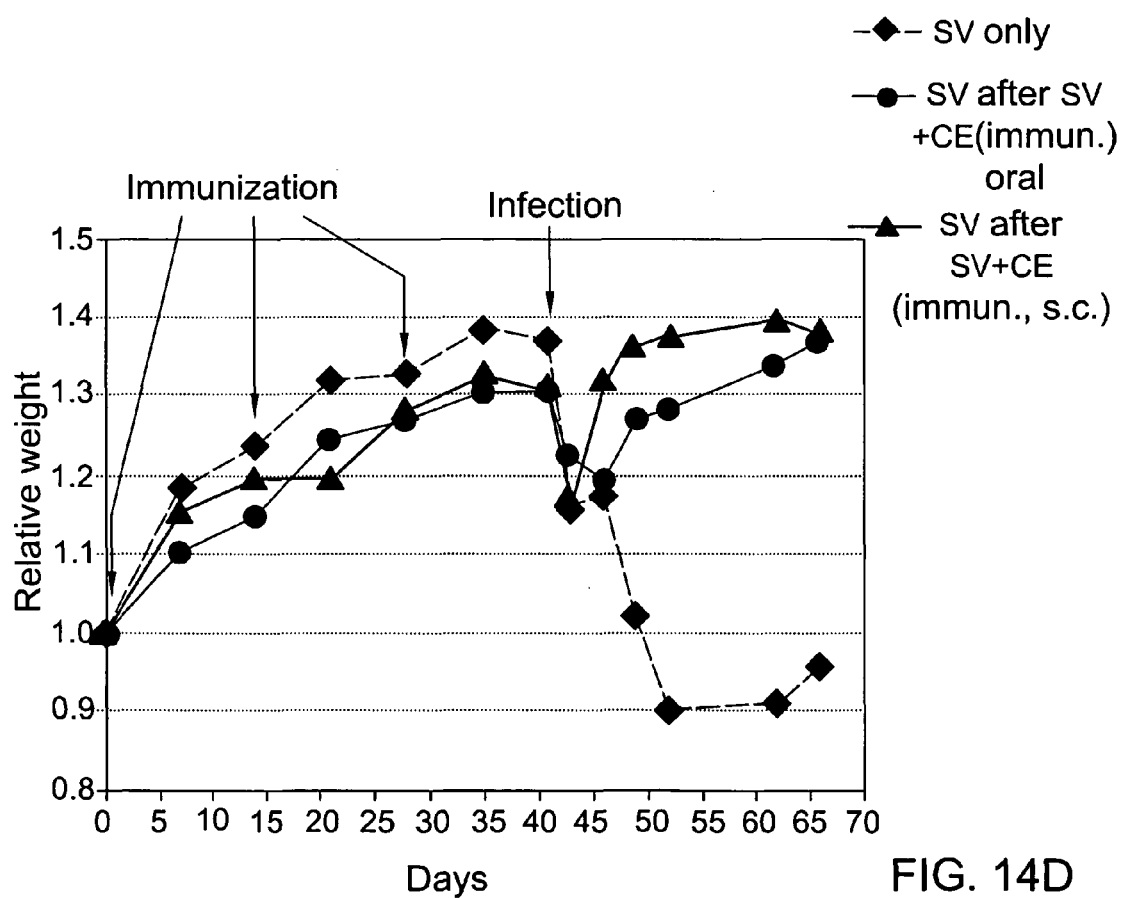
FIG. 14(d) depicts changes in weight of mice immunized orally or s.c. with Sendai virus and the inhibitor before infecting the mice with naïve Sendai virus.

Similarly, two groups of mice were immunized 3 times by the Sendai virus mixed with the CE ppt inhibitor via two different routes of administration: oral and subcutaneously (s.c) as shown in FIG. 14d. Two weeks after the third administration of the virus plus the CE ppt, the mice of both groups were infected with 80 HAU of the naïve virus, as were the mice of the control group. The immunized mice were not affected by the subsequent virus infection and continued gaining weight. Basically, no difference was observed between the mice to which the virus plus the CE ppt were administered orally or the mice which were administered s.c (P=<0.001).

EXAMPLE 13

Inhibition of HIV-1

Figure 15A:
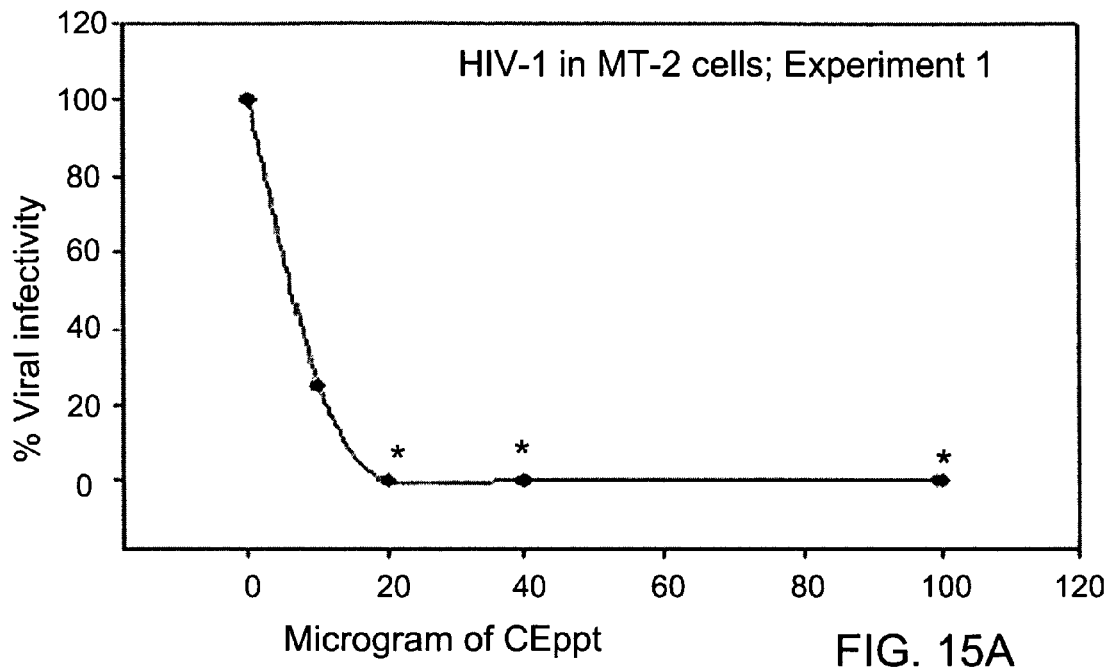
FIG. 15(a-b) depicts the inhibition of HIV-1 activity tested on MT2 cells in two different experiments.

HIV-1 activity was tested on MT2 cells (CD4+ T-cells) using the model of syncytia formation in cell culture. 20-120 μl aliquots of the VNF (CEppt) fraction, 0.5 mg/ml, were incubated with 50 μl virus for 5 minutes in a final volume of 200 μl RPMI medium at room temperature. 90 μl of each mixture were added onto the cells in duplicates. After 3 days of incubation at 37° C. in a 5% $CO_2$ humidified incubator, the infectivity was determined by monitoring syncytia formation. Syncytia were observed in 95-100% of the control wells without CEppt and served as the 100% infectivity to which other wells were compared. As shown in FIGS. 15A and B, 8-10 μg of CEppt in 8-10 μl was sufficient to neutralize the virus completely.

EXAMPLE 14

Inhibition of Avian Influenza H9N2 by VNF (CE ppt)

The inhibition of avian influenza H9N2 by VNF was tested by the in vitro Hemolysis Assay as done previously (Borkow and Ovadia, 1994, 1999). The hemolytic activity of the influenza virus (release of hemoglobin from red blood cells) was examined on human erythrocytes as follows: Human blood was obtained from the Blood Bank and was used fresh. Prior to use, erythrocytes were washed 5 times with Phosphate Buffered Saline (PBS), pH 7 and diluted to a concentration of 4%, with the same buffer. The washed diluted erythrocytes were mixed with the virus alone or with a virus preincubated with the Viral Neutralizing Fraction (VNF) for 20 minutes at room temperature. After the attachment, excess virus was removed by washing with PBS before adding 200 μl of 0.1 M sodium citrate buffer at pH 4.6 for three min., in order to achieve fusion of the virus with the erythrocytes. The mixture was then washed in PBS, centrifuged and incubated in 0.8 ml PBS at 37° C. for 3 hours. Intact erythrocytes were removed by centriftigation and 300 μl aliquot was withdrawn from the supernatant of each sample into wells of an ELISA plate for measurement of the absorbance in an ELISA plate reader at 540 nm. Release of hemoglobin into the measured supernatant indicates viral hemolytic activity.

Figure 16:
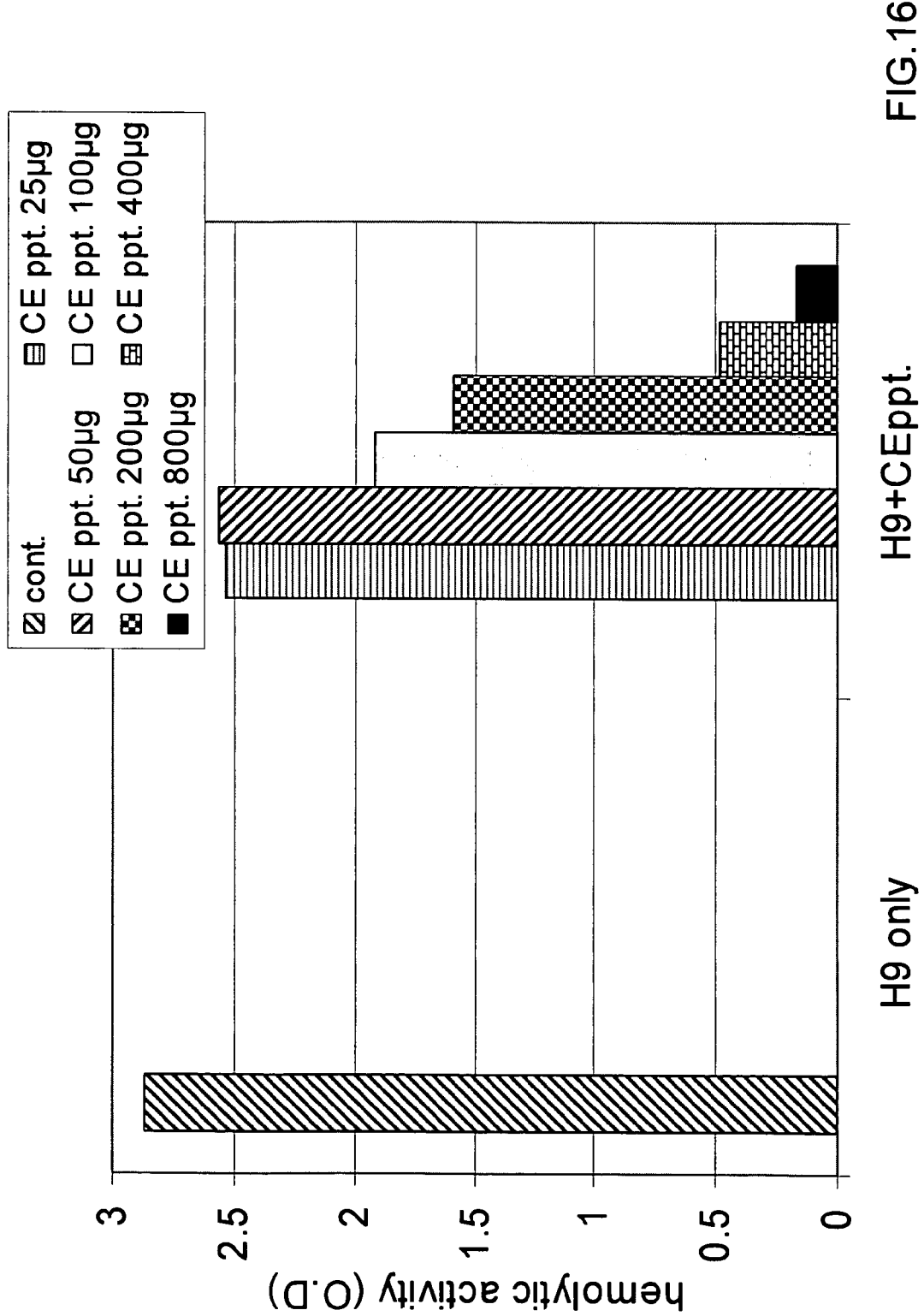
FIG. 16 depicts the inhibition of avian influenza H9N2 by VNF (CE ppt)

As FIG. 16 shows, the hemolytic activity of the virus was neutralized by the VNF (CEppt) in a dose dependent manner.

EXAMPLE 15

Inhibition of Preabsorbed Avian Influenza H9N2 by VNF (CEppt)

Figure 17:
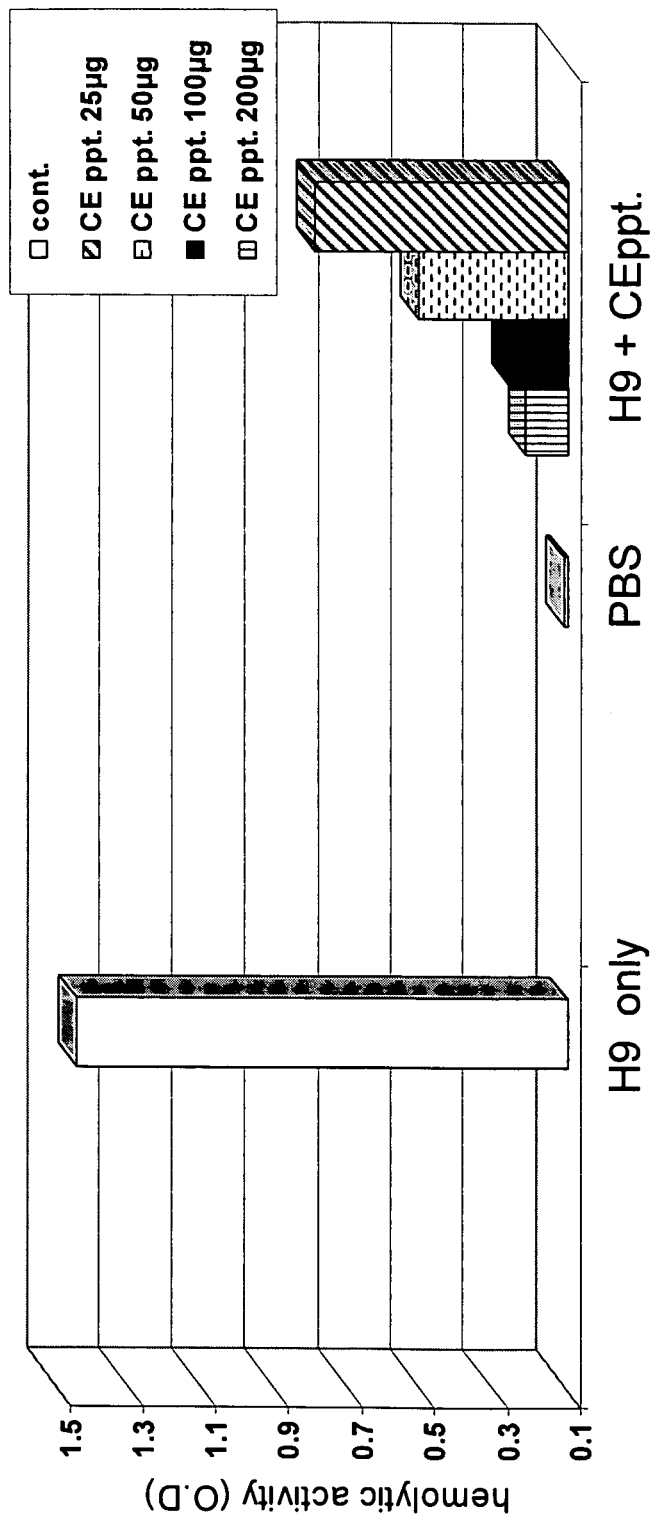
FIG. 17 depicts the inhibition of preabsorbed avian influenza H9N2 by VNF (CE ppt)

Influenza H9N2 virus was absorbed onto human erythrocytes at room temperature before application of VNF (CEppt) on the infected cells. The cells were then incubated at 37° C. and the hemolytic activity was determined as described in a previous figure. As FIG. 17 shows, CEppt inhibited the hemolytic activity of the avian influenza virus after it was attached on the infected cells as it did to the free virus.

EXAMPLE 16

Inhibition of NDV Hemagglutinating Activity by VNF

Figure 18:
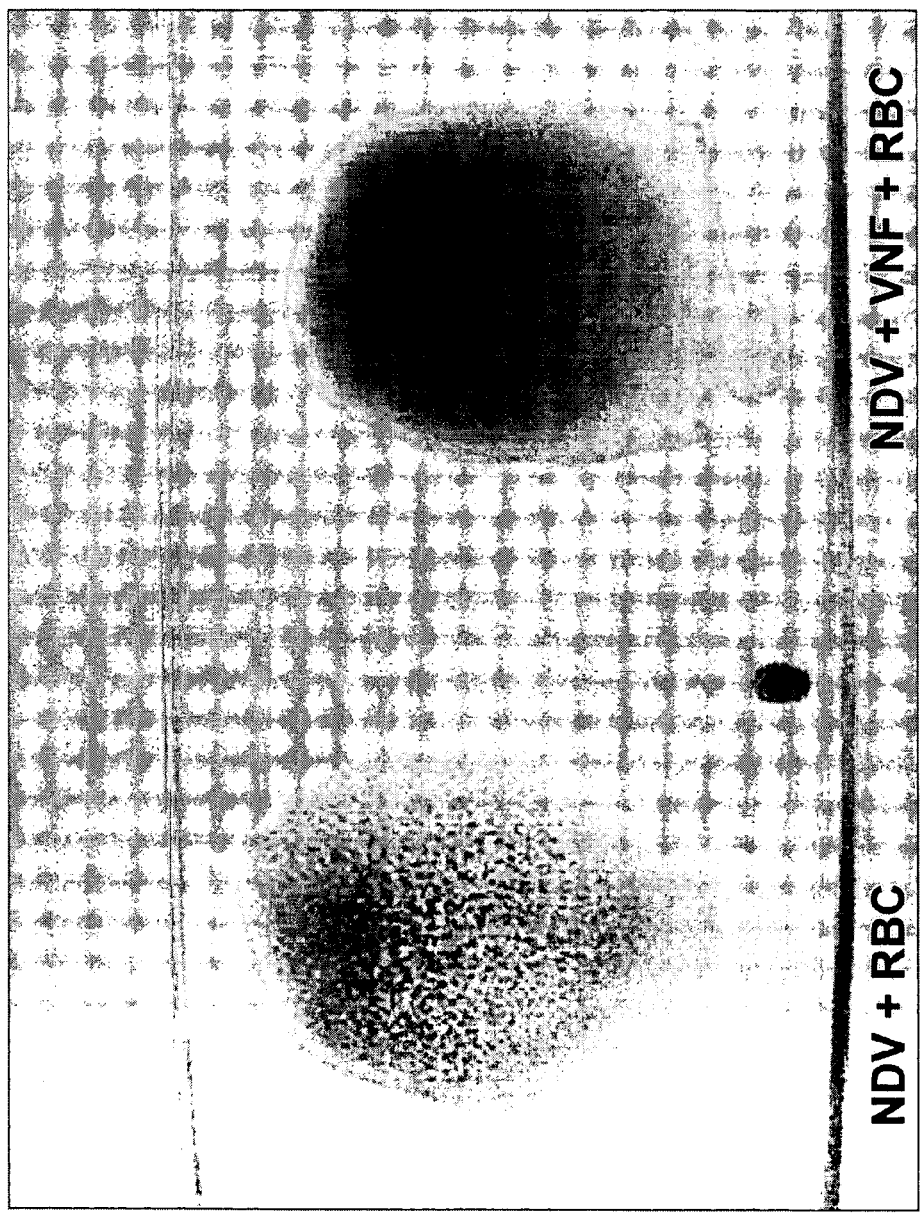
FIG. 18 depicts the inhibition of the hemagglutinating activity of NDV by VNF.

Hemagglutinating activity of the Newcastle Disease virus (NDV) was tested by mixing a drop of chicken blood with a drop of the virus suspended in PBS on a microscope slide (left side of the picture). As shown in FIG. 18, right hand-side picture, preincubation of the virus ($10^8$ $EID_{50}$) with 10 mg of VNF (CEppt) resulted in Hemagglutination Inhibition. No such HI was observed in the absence of the NVF (left hand-side picture).

EXAMPLE 17

In-vivo (In-ova) Neutralization of Avian Influenza H9N2 by VNF

Figure 15B:
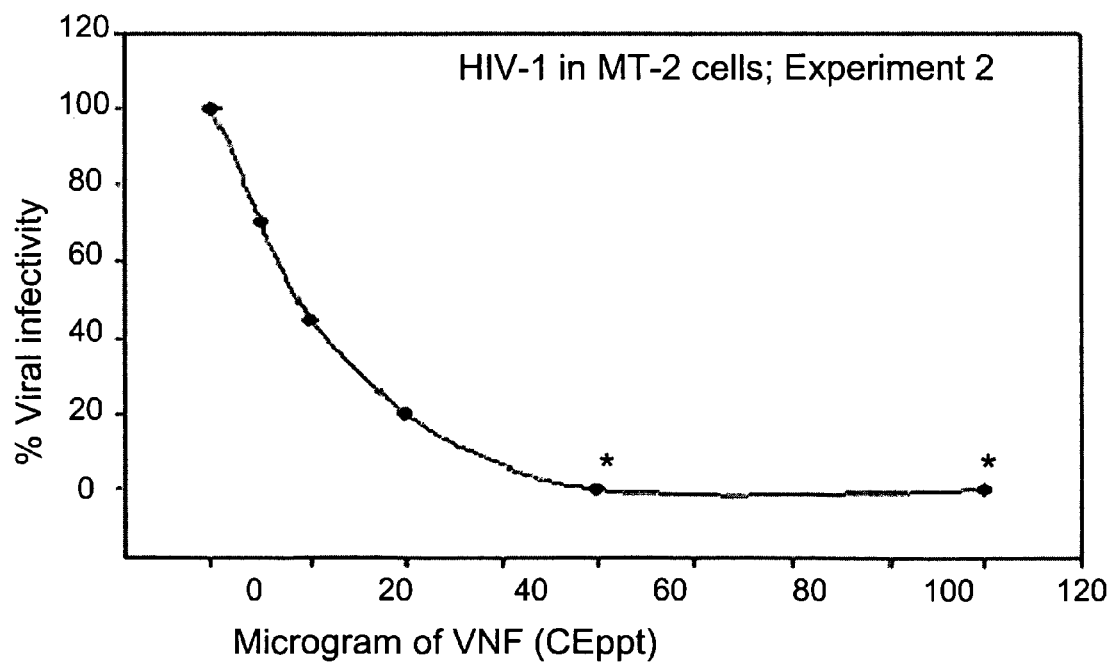
Figure 19A:
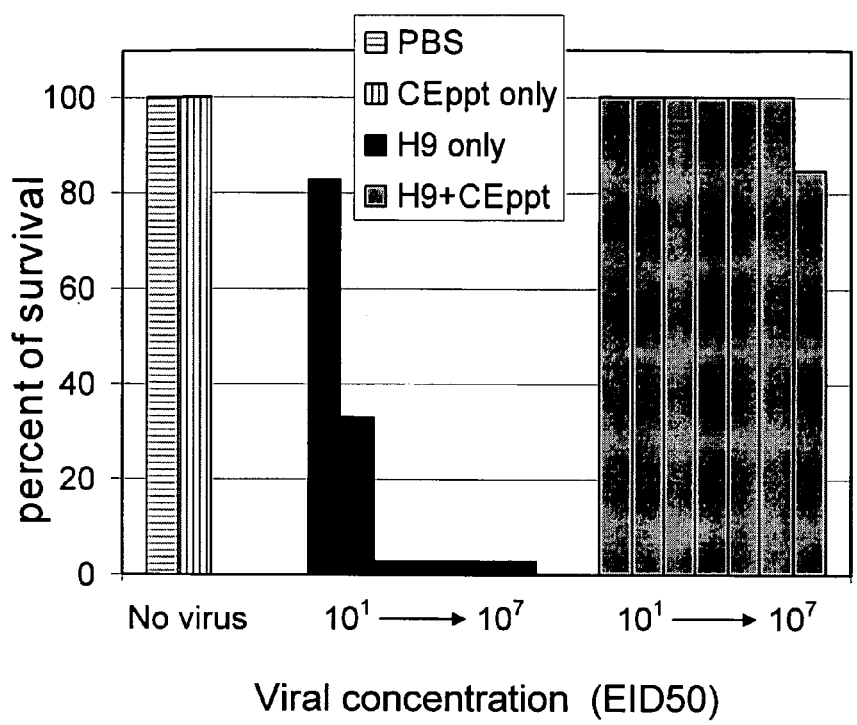
FIG. 19(a-b) depicts in vivo neutralization and inhibition of influenza H9N2 by VNF (CE ppt)
Figure 19B:
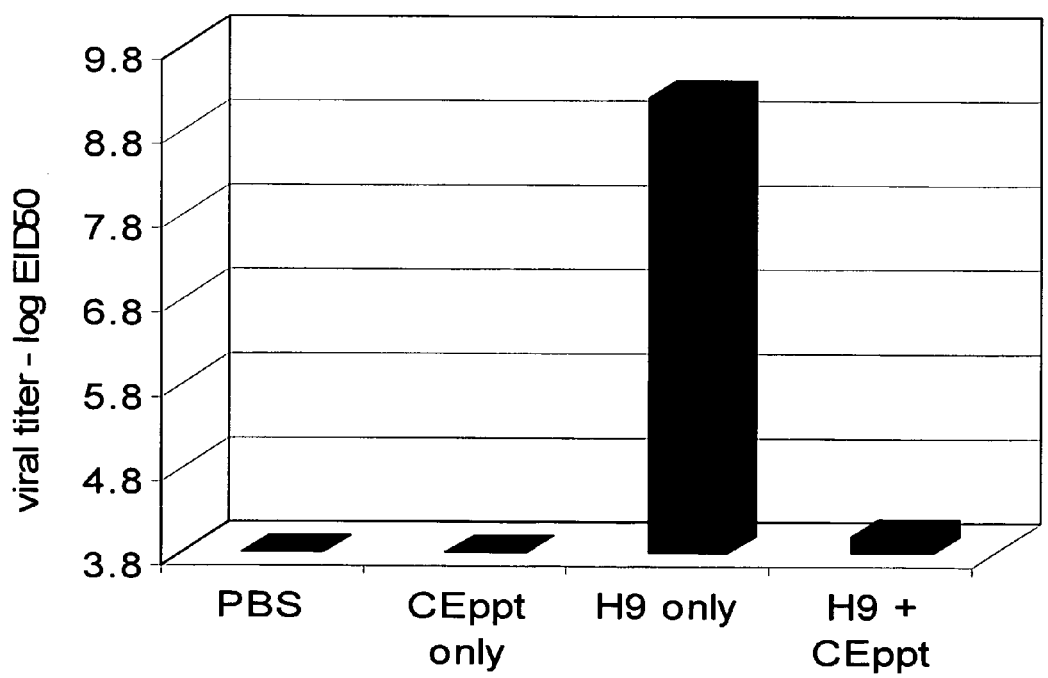

One ml containing 4.5 mg of VNF (CEppt) and $10^7$ $EID_{50}$ of influenza H9N2 were incubated for 20 minutes at room temperature before preparing 10 fold dilutions from this mixture. 0.1 ml of each dilution was injected into each allantoic cavity of 10 embryonated chicken SPF eggs, 11 days old. Same dilutions of the virus alone or VNF alone were used as controls (10 eggs in each group). The eggs were observed during the following week for vitality and viral hemagglutinating activity. As FIGS. 19A and B demonstrate, VNF decreased the viral infectivity by 5 logs (FIG. 15B) and increased the survival of the embryos at the similar rate (FIG. 19A).

EXAMPLE 18

In-vivo Neutralization of Newcastle Disease Virus by VNF

Figure 20A:
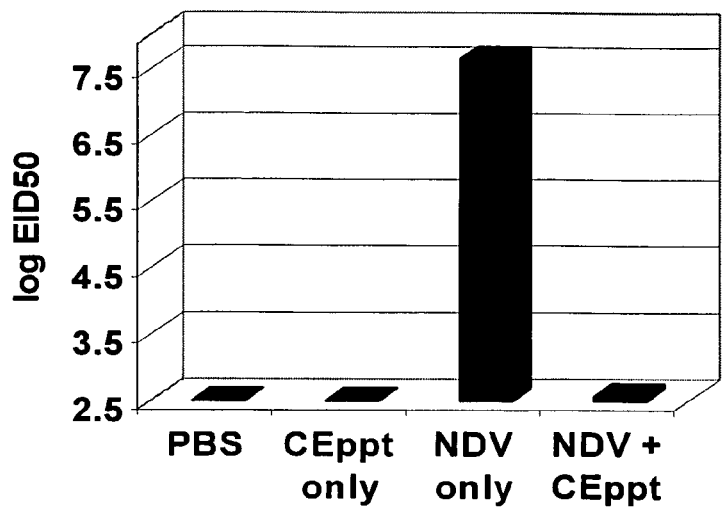
FIG. 20(a-b) depicts in vivo inhibition and neutralization of Newcastle Disease Virus (VNF) by VNF (CEppt)
Figure 20B:
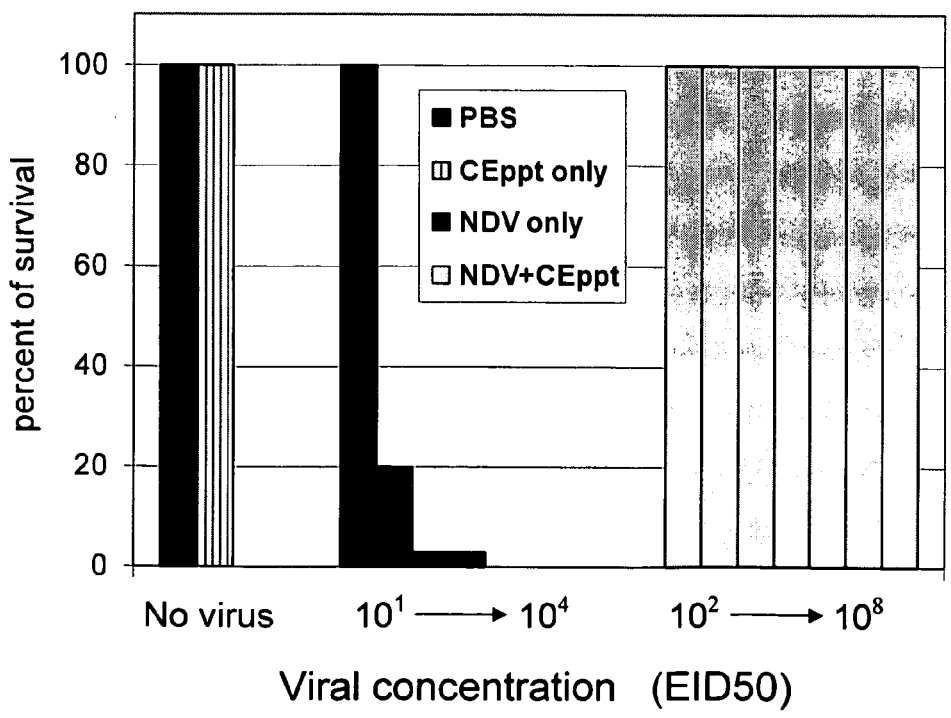

This experiment is similar to the previous one carried out with the avian influenza H9N2. One ml containing 5 mg of VNF (CEppt) and $10^8$ $EID_{50}$ of Newcastle Disease Virus were incubated for 20 minutes at room temperature before preparing 10 fold dilutions from this mixture. 0.1 ml of each dilution was injected into each allantoic cavity of 10 chicken SPF eggs (11 days old). Same dilutions of the virus alone or VNF alone were used as controls (10 eggs in each group). The eggs were observed during the following week for vitality and viral hemagglutinating activity. As FIGS. 20A and B demonstrate, VNF decreased the viral infectivity by 5 logs and increased the survival of the embryos at the similar rate.

EXAMPLE 19

Figure 21:
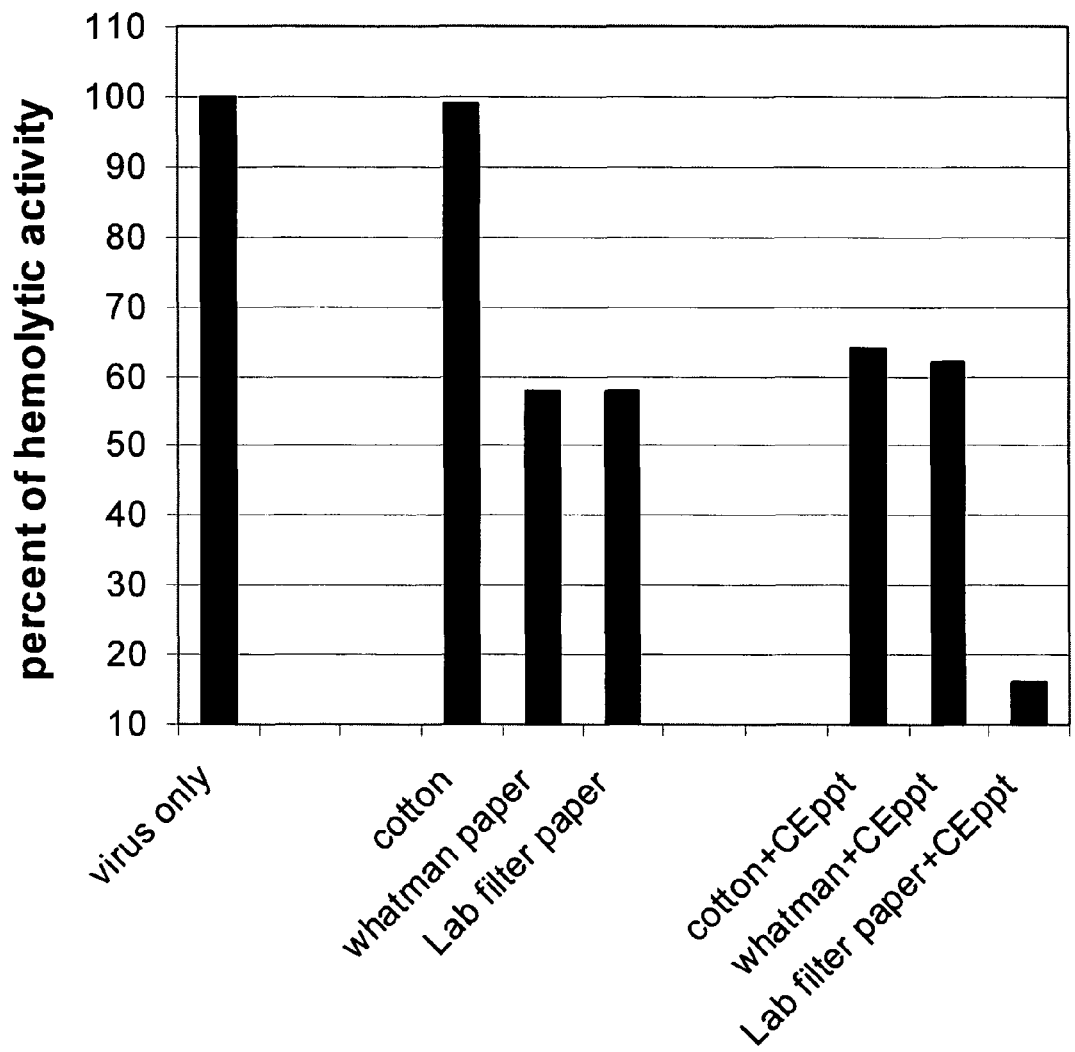
FIG. 21 shows the development of filters for decreasing influenza activity.

Development of Filters for Decreasing Influenza Activity 0.5 ml containing 2.5 mg of VNF (CEppt) were absorbed onto 250 mg of each three filtering materials (names on the graph) and dried overnight at room temperature. 1 ml of human influenza H1N1 virus containing 1280 HAU was filtered through each one, and the passing fluid was tested for hemolytic activity on washed human erythrocytes as described above. As FIG. 21 demonstrates, the lab filter paper absorbed with the CEppt was most efficient in absorbing the VNF and reduced the hemolytic activity of the filtered virus significantly.

EXAMPLE 20

Serum Titer of Chicks Following Vaccination with NDV+CEppt

Two different approaches of vaccination were used: Vaccination in-ovo was compared with the customary intraocular vaccination of 1-2 day old chicks. In-ovo vaccination of the first group was carried out by injecting 0.1 ml of PBS containing $10^{5.3}$ $EID_{50}$ of NDV preincubated with 1 mg of VNF into SPF chicken eggs at day 18 of the embryonic development. Second group was vaccinated 1-2 days after hatching by dripping the same dose into the eyes of the chicks (the customary intraocular vaccination). Non-vaccinated chicks were used as controls. Blood samples were withdrawn from each chick at days 7, 14, 24 post-vaccination and the serum titer was determined by hemagglutination inhibition assay of serial dilutions of each serum.

The serum titer after in-ovo vaccination was as good as the tedious customary intraocular vaccination of 1-2 day old chicks. In-ovo vaccination was much more comfortable and safe.

TABLE

Serum titer of chicks following vaccination with NDV + CEppt

| Group | Average Serum Titer (Hemagglutination Inhibition) | | |
|---|---|---|---|
| | Day 7 | Day 17 | Day 24 |
| in-ovo (D18) NDV + CEppt | 7.6 ± 0.5 | 9.2 ± 0.8 | 9.0 ± 0.1 |
| intraocular (D2) NDV only | 4.0 ± 1.0 | 8.1 ± 1.0 | 8.7 ± 0.7 |
| non-vaccinated | 2.0 ± 0.1 | 1.9 ± 0.2 | 3.1 ± 0.2± |

LIST OF REFERENCES

American Lung Association, Jan. 8, 2002. Flu and Cold: Statistics.

Hernandez et al., (2004). Influence of two plant extracts on broilers performance, digestibility, and digestive organ size, *Poult. Sci.*, 83(2):169-74.

Kalemba and Kunicka, (2003). Antibacterial and antifungal properties of essential oils, *Curr. Med. Chem.*, 10(10):813-29.

Khan et al, (2003). Cinnamon improves glucose and lipids of people with type 2 diabetes, *Diabetes Care*, 26:3215-3218.

Lay nd Roy, (2004). Antimicrobial and chemo-preventive properties of herbs and spices, *Curr. Med. Chem.*, 11(11):1451-60.

Mau, J. L., et al., (2001). Antimicrobial effect of extracts from Chineese Chive, Cinnamon, and Corni fructus. *J. Agric. Food Chem.* 49:183-188.

Murcia et al, (2004). Antioxidant evaluation in dessert spices compared with common food additives, influence of irradiation procedure, *J. Agric. Food Chem.*, 52:1872-1881.

Qin et al., (2004), Cinnamon extract prevents the insulin resistance induced by a high fructose diet, *Horm. Metab. Res.*, 35:119-125.

Singh, H. B. et al., (1995), cinnamon bark oil, a potent fungitoxicant against fungi causing respiratory tract mycoses. Allergy, 50(12): 995-999.

Steinhaur, D. A., Wharton, S. A., Skehel, J. J., Wiley, D. C. and Hay, A. J. (1991). Amantadine selection of a mutant influenza virus containing an acid stable hemagglutinin glycoprotein: evidence for virus specific regulation of the pH of glycoprotein transport vesicles. Proc. Natl. Acad. Sci. U.S.A., 88: 11525-11529.

Tabak, M. et al., (1999). Cinnamon extracts' inhibitory effect on *Helicobacter pylori*, *J. Ethnopharmacol.* 67:269-277.

Usta et al., (2003). Comparative study on the effect of cinnamon and clove extracts and their main components on different types of ATPases, *Hum. Exp. Toxicol.*, 22(7):355-62.

Valero and Salmeron, (2003). Antibacterial activity of 11 essential oils against *Bacillus cereus*, in tyndallized carrot broth. *Intl. J. of Food Microbiology*, 85: 73-81.

Velluti et al., (2004). Impact of essential oils on growth rate, zearalenone and deoxynivalenol production by *Fusarium graminearum* under different temperature and water activity conditions in maize grain, *J. of Applied Microbiology*, 96: 716-724.)

Velluti et al., (2003). Inhibitory effect of cinnamon, clove, lemongrass, oregano and palmarose essential oils on growth and fumonisin B1 production by *Fusarium proliferatum* in maize grain. *Intl. J. of Food Microbiology*, 89:145-154.

W.H.O. Influenza, Fact Sheet No. 211, March 2003.

W.H.O. Global Influenza Programme, Note for the Press No. 22, September 2003.
W.H.O. Avian influenza, January 2004.
W.H.O. H5N1 avian influenza: a chronology of key events, February 2004.
W.H.O. Avian influenza A (H7) human infections in Canada, April 2004.
W.H.O. Working Group Three: Antivirals—their use and availability, April 2004.
W.H.O. Assessment of risk to human health associated with outbreaks of highly pathogenic H5N1 avian influenza in poultry, May 2004.
Yamasaki et al., (1998), anti-HIV-1 activity of herbs in Labiatae. *Biol. Pharm. Bull.*, 21:829-8339.
Borkow et al., (1994), Echinibin-1—an inhibitor of Sendai virus isolated from the venom of the snake *Echis coloratus*. Antiviral Research 23:161-76.
Borkow et al., (1999), Selective lysis of virus infected cells by cobra snake cytotoxins. Biochemical and Biophysical Research Communication, 264:63-8.

The invention claimed is:

1. A composition which is (1) an aqueous extract of cinnamon bark (*Cinnamon* sp.), (2) a precipitate of said aqueous extract or (3) a fraction of said extract or precipitate; said extract, precipitate or fraction comprising an active fraction, said active fraction having an absorbance at 280 nm of between 15 and 20 OD, and comprising at least one substance having a molecular weight greater than 10 kDa and antiviral activity.

2. The composition according to claim 1, wherein said active fraction having an absorbance at 280 nm at about 15 OD.

3. The composition according to claim 1 obtained by a process comprising:
   (i) grinding cinnamon bark into powder;
   (ii) stirring the powder into an aqueous buffer to obtain a solution;
   (iii) centrifuging the solution and collecting a supernatant comprising said active fraction; and
   (iv) optionally, adding a salt to the supernatant to obtain said fraction as a precipitate.

4. The composition according to claim 3, wherein the process further comprises:
   (v) dissolving the precipitate in water or buffer at an essentially neutral pH to obtain a precipitate solution;
   (vi) separating the precipitate solution on a SEPHAROSE column; and
   (vii) eluting the SEPHAROSE column with buffer and a saccharide.

5. The composition according to claim 3, wherein the salt is a chloride salt.

6. The composition according to claim 5, wherein the chloride salt is selected from the group consisting of KCl, NaCl, $MgCl_2$, $SrCl_2$, $CuCl_2$, and $ZnCl_2$.

7. The composition according to claim 1, said composition obtained by a process comprising:
   (i) grinding cinnamon bark into powder;
   (ii) stirring the powder into a 0.02M aqueous phosphate buffer at a pH of 7.0 to obtain a solution;
   (iii) centrifuging the solution and collecting a supernatant comprising crude neutralizing extract (CE);
   (iv) precipitating an active antiviral material from the crude extract comprising adding 0.15M KCl or 0.08M $MgCl_2$ to obtain a precipitate;
   (v) dissolving the precipitate in water or 0.01M phosphate buffer at pH 7.0 to obtain a precipitate solution;
   (vi) loading the precipitate solution onto a SEPHAROSE 4B column followed by a stepwise elution with phosphate buffer and galactose; and
   (vii) collecting one or more fractions, wherein the active antiviral material elutes from the column with 0.15M galactose, and at least one active fraction so eluted is collected.

8. A composition comprising an effective amount of the composition according to claim 1 and a pharmaceutically or nutraceutically acceptable carrier.

9. The composition according to claim 1, wherein the antiviral activity is against infections caused by an enveloped virus.

10. The composition according to claim 9, wherein the enveloped virus is selected from the group consisting of Orthomyxoviruses, Paramyxoviruses, Herpesviruses, Retroviruses, Coronaviruses, Hepadnaviruses, Poxviruses, Togaviruses, Flaviviruses, Filoviruses, Rhabdoviruses, and Bunyaviruses.

11. The composition according to claim 10, wherein the virus is selected from the group consisting of NDV virus, avian influenza virus, Influenza, Parainfluenza virus, HIV virus and HSV-1 virus.

12. The composition according to claim 11, wherein the virus is the HIV virus.

13. The composition according to claim 11, wherein the virus is an avian influenza virus.

14. The composition according to claim 11, wherein the virus is NDV.

15. The composition of claim 1 wherein the composition comprises a substance having antiviral activity against a virus other than HIV.

16. The composition of claim 1 wherein the antivirally active substance is resistant to acid but at least partially inactivated by base.

17. The composition of claim 1 wherein the active substance is precipitable by addition of a chloride salt to said extract, and is elutable by 0.15M galactose from a Sepharose 4B column prewashed with phosphate buffer 0.01M at pH 7.

18. A filter containing or absorbed with an effective amount of the composition according to claim 1.

19. A method for the treatment of a viral infection comprising administering to a subject in need thereof a therapeutically effective amount of the composition according to claim 1.

20. The method according to claim 19, wherein the viral infection is caused by an enveloped virus.

21. The method according claim 20, wherein the enveloped virus is selected from the group consisting of Orthomyxoviruses, Paramyxoviruses, Herpesviruses, Retroviruses, Coronaviruses, Hepadnaviruses, Poxviruses, Togaviruses, Flaviviruses, Filoviruses, Rhabdoviruses, and Bunyaviruses.

22. The method according to claim 21, wherein the virus is selected from the group consisting of Influenza, Parainfluenza virus, and HSV-1 virus.

23. The method according to claim 22, wherein the virus is HIV virus.

24. The method according to claim 22, wherein the virus is an avian influenza virus.

25. The method according to claim 22, wherein the virus is NDV.

26. The method of claim 21, wherein the extract is administered orally.

27. The method of claim 21, wherein the extract is administered nasally.

28. The method according to claim 21, wherein the extract is administered parenterally.

29. The method according to claim 21, wherein the extract is administered subcutaneously.

30. The method according to claim 21, wherein the extract is administered intramuscularly.

31. A method for disinfecting an area suspected of being contaminated with viruses, comprising applying on to the suspected area an effective amount of the composition according to claim 1.

32. The method of claim 31, wherein the area is any surface in a house or in a medical facility.

33. The method of claim 31, wherein disinfecting comprises passing air through appropriate filters containing or absorbed with an effective amount of the composition according to claim 1.

34. The method according to claim 33, wherein the filters are mounted in airplanes, hospitals, kindergartens, offices, and/or homes.

35. A method for producing a neutralized virus for immunization comprising contacting native viruses with an effective amount of the composition according to claim 1.

36. The method according to claim 35, wherein the neutralized virus is selected from the group consisting of Orthomyxoviruses, Paramyxoviruses, Herpesviruses, Retroviruses, Coronaviruses, Hepadnaviruses, Poxviruses, Togaviruses, Flaviviruses, Filoviruses, Rhabdoviruses, and Bunyaviruses.

37. The method of claim 36, wherein the native virus is selected from the group consisting of NDV, influenza, avian influenza, Parainfluenza, HIV-1, and HSV-1.

38. A neutralized virus prepared by the method of claim 35.

39. A vaccine formulation comprising the neutralized virus of claim 38.

40. A method of immunizing against a viral infection comprising administering to an effective amount of the subject a neutralized virus according to claim 38.

41. A method of immunizing against a viral infection comprising administering to an effective amount of the subject a vaccine formulation according to claim 39.

* * * * *